United States Patent
Menke et al.

(10) Patent No.: US 6,268,311 B1
(45) Date of Patent: Jul. 31, 2001

(54) 1-AMINO-3-BENZYLURACILS

(75) Inventors: Olaf Menke, Altleiningen; Ralf Klintz, Gruenstadt; Gerhard Hamprecht, Weinheim; Elisabeth Heistracher, Ludwigshafen; Peter Schäfer, Ottersheim; Cyrill Zagar, Ludwigshafen; Norbert Götz, Worms; Karl-Otto Westphalen, Speyer; Ulf Misslitz, Neustadt; Helmut Walter, Obrigheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 08/981,049

(22) PCT Filed: Jun. 20, 1996

(86) PCT No.: PCT/EP96/02666

§ 371 Date: Mar. 17, 1998

§ 102(e) Date: Mar. 17, 1998

(87) PCT Pub. No.: WO97/01543

PCT Pub. Date: Jan. 16, 1997

(30) Foreign Application Priority Data

Jun. 29, 1995 (DE) .............................................. 195 23 372

(51) Int. Cl.$^7$ ........................ C07D 239/545; A01N 43/54
(52) U.S. Cl. .......................... 504/243; 544/310; 544/311; 544/312; 544/2; 544/53; 544/54; 544/55; 544/65; 540/544; 540/601; 504/219; 504/221; 504/223

(58) Field of Search ..................................... 504/243, 219; 544/310, 311, 312, 2, 53, 54, 55, 65; 540/544

(56) References Cited

FOREIGN PATENT DOCUMENTS

95/0441   2/1995   (WO) .

Primary Examiner—John M. Ford
(74) Attorney, Agent, or Firm—Keil & Weinkauf

(57) ABSTRACT

1-Amino-3-benzyluracils I

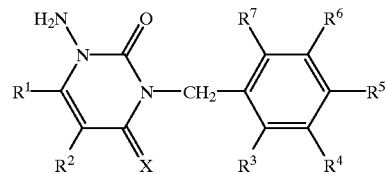

(X=oxygen, sulfur;

$R^1$=$C_1$–$C_4$-haloalkyl;

$R^2$=H, halogen; $R^3$, $R^7$=H, CN, SCN, halogen, $C_1$–$C_4$-haloalkyl, $C_1$–$C_4$-haloalkoxy, $C_1$–$C_4$-haloalkylthio;

$R^4$=H, CN, SCN, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-haloalkylthio, $C_1$–$C_6$-alkylaminocarbonyl;

$R^5$=H, CN, $NO_2$, halogen, OH, $C_1$–$C_4$-alkoxy, $NH_2$, $C_1$–$C_6$-alkyl-amino;

$R^6$=H, CN, $NO_2$, halogen, OH, $C_1$–$C_4$-alkoxy, $NH_2$, $C_1$–$C_6$-alkyl-amino, CHO)

and their salts are used as herbicides and for the desiccation/defoliation of plants.

16 Claims, No Drawings

1-AMINO-3-BENZYLURACILS

The present invention relates to 1-amino-3-benzyluracils of the formula I

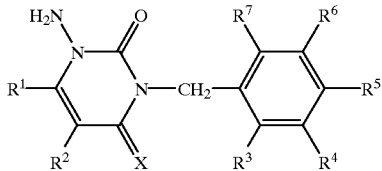

where the variables have the following meanings:
  X is oxygen or sulfur;
  $R^1$ is $C_1$–$C_4$-haloalkyl;
  $R^2$ is hydrogen or halogen;
  $R^3$ and $R^7$ independently of one another are hydrogen, cyano, thiocyanato, halogen, $C_1$–$C_4$-haloalkyl, $C_1$–$C_4$-haloalkoxy or $C_1$–$C_4$-haloalkylthio;
  $R^4$ is hydrogen, cyano, thiocyanato, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-haloalkylthio or $C_1$–$C_6$-alkylaminocarbonyl;
  $R^5$ is hydrogen, cyano, nitro, halogen, hydroxyl, $C_1$–$C_4$-alkoxy, amino or $C_1$–$C_6$-alkylamino; and
  $R^6$ is hydrogen, cyano, nitro, halogen, hydroxyl, $C_1$–$C_4$-alkoxy, amino, $C_1$–$C_6$-alkylamino or formyl;
and to the agriculturally useful salts of the compounds I.
  The invention furthermore relates to
  the use of the compounds I as herbicides and/or for the desiccation and/or defoliation of plants,
  herbicidal compositions and compositions for the desiccation and/or defoliation of plants, which comprise the compounds I as active ingredients,
  processes for the preparation of the compounds I and of herbicidal compositions and compositions for the desiccation and/or defoliation of plants using the compounds I,
  methods of controlling undesirable vegetation and for the desiccation and/or defoliation of plants using the compounds I, and
  novel intermediates of the formulae III and IV.
  3-Benzyl-1-methyl-6-trifluoromethyluracils of the formula II

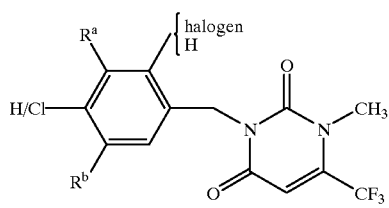

where
  $R^a$ is hydrogen, cyano, halogen, lower alkoxy, lower alkylaminocarbonyl or propargyloxy and
  $R^b$ is hydrogen, cyano, halogen, lower alkylaminocarbonyl or carboxyl
are described as herbicides in WO 95/04461.
  However, the herbicidal action, against the harmful plants, of the known compounds is not always entirely satisfactory.

Accordingly, it was an object of the present invention to provide novel herbicidally active compounds with which targeted control of undesirable plants can be effected better than has been possible to date. Another object is to provide novel compounds which act as desiccants/defoliants.
  Accordingly, we have found that this object is achieved by the 1-amino-3-benzyluracils of the formula I defined at the outset. We have furthermore found herbicidal compositions which comprise the compounds I and which have a very good herbicidal action. Moreover, we have found processes for the preparation of thees compositions and methods of controlling undesirable vegetation using the compounds I.
  Furthermore, we have found that the compounds I are also suitable for the defoliation and desiccation of parts of plants, suitable plants being crop plants such as cotton, potatoes, oilseed rape, sunflowers, soya beans or faba beans, in particular cotton. Thus, we have found compositions for the desiccation and/or defoliation of plants, processes for the preparation of these compositions and methods for the desiccation and/or defoliation of plants using the compounds I.
  Depending on the substitution pattern, the compounds of the formula I can have one or more chiral centers, in which case they are present as enantiomers or diastereomer mixtures. The invention also relates to the pure enantiomers or diastereomers and also to their mixtures.
  Suitable amongst the agriculturally useful salts are, especially, the salts of those cations or the acid addition salts of those acids whose cations or anions do not adversely affect the herbicidal action of the compounds I. Thus, suitable cations are, in particular, the ions of the alkali metals, preferably sodium and potassium, of the alkaline earth metals, preferably calcium, magnesium and barium, and of the transition metals, preferably manganese, copper, zinc and iron, and the ammonium ion which, if desired, can have attached to it one to four $C_1$–$C_4$-alkyl substituents and/or a phenyl or benzyl substituent, preferably diisopropylammonium, tetramethylammonium, tetrabutylammonium, trimethylbenzylammonium, furthermore phosphonium ions, sulfonium ions, preferably tri($C_1$–$C_4$-alkyl)sulfonium and sulfoxonium ions, preferably tri($C_1$–$C_4$-alkyl)sulfoxonium.
  Anions of useful acid addition salts are, mainly, chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$–$C_4$-alkanoic acids, preferably formate, acetate, propionate and butyrate.
  With a view to the use of the compounds of the formula I according to the invention as herbicides and/or as compounds which act as defoliants/desiccants, the variables preferably have the following meanings, in each case on their own or in combination:
  X is oxygen;
  $R^1$ is trifluoromethyl;
  $R^2$ is hydrogen;
  $R^3$ is chlorine;
  $R^4$ is hydrogen, cyano, halogen, $C_1$–$C_4$-alkoxy or $C_1$–$C_3$-alkylaminocarbonyl; and
  $R^7$ is hydrogen.
  The organic moieties mentioned for the substituents $R^1$, $R^3$, $R^4$ and $R^7$ are collective terms for individual enumerations of the individual group members. All carbon chains, i.e. all alkyl, haloalkyl, alkoxy, haloalkoxy, haloalkylthio and alkylaminocarbonyl moieties, can be straight-chain or branched. Unless otherwise indicated, halogenated substituents preferably have attached to them one to five identical or different halogen atoms. The meaning halogen represents in each case fluorine, chlorine, bromine or iodine.

Further meanings are, for example, $C_1$–$C_4$-alkyl: methyl, ethyl, n-propyl, 1-methylethyl, n-butyl, 1-methylpropyl, 2-methylpropyl or 1,1-dimethylethyl, in particular methyl or ethyl;

$C_1$–$C_4$-haloalkyl: a $C_1$–$C_4$-alkyl radical as mentioned above which is partially or fully substituted by fluorine, chlorine, bromine and/or iodine, e.g. chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl, in particular trifluoromethyl or 1,2-dichloroethyl;

$C_1$–$C_4$-alkoxy: methoxy, ethoxy, n-propoxy, 1-methylethoxy, n-butoxy, 1-methylpropoxy, 2-methylpropoxy or 1,1-dimethylethoxy, in particular methoxy, ethoxy, 1-methylethoxy or 1,1-dimethylethoxy;

$C_1$–$C_4$-haloalkoxy: $C_1$–$C_4$-alkoxy as mentioned above which is partially or fully substituted by fluorine, chlorine and/or bromine, e.g. chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, bromodifluoromethoxy, 1-fluoroethoxy, 2-fluoroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy, preferably difluoromethoxy, trifluoromethoxy or pentafluoroethoxy;

$C_1$–$C_4$-alkylthio: methylthio, ethylthio, n-propylthio, 1-methylethylthio, n-butylthio, 1-methylpropylthio, 2-methylpropylthio or 1,1-dimethylethylthio, in particular methylthio or ethylthio;

$C_1$–$C_4$-haloalkylthio: $C_1$–$C_4$-alkylthio as mentioned above which is partially or fully substituted by fluorine, chlorine and/or bromine, e.g. difluoromethylthio, trifluoromethylthio, chlorodifluoromethylthio, bromodifluoromethylthio, 2-fluoroethylthio, 2-chloroethylthio, 2-bromoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio or 4-bromobutylthio;

$C_1$–$C_6$-alkylamino and the alkylamino moiety of $C_1$–$C_6$-alkylaminocarbonyl: methylamino, ethylamino, n-propylamino, 1-methylethylamino, n-butylamino, 1-methylpropylamino, 2-methylpropylamino, 1,1-dimethylethylamino, n-pentylamino, 1-methylbutylamino, 2-methylbutylamino, 3-methylbutylamino, 1,1-dimethylpropylamino, 1,2-dimethylpropylamino, 2,2-dimethylpropylamino, 1-ethylpropylamino, n-hexylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino or 1-ethyl-2-methylpropylamino.

The 1-amino-3-benzyluracils of the formula I can be obtained by various routes, in particular by one of the following processes:

Process A)

Cyclization of an enamino ester of the formula III or of an enamine carboxylate of the formula IV in the presence of a base:

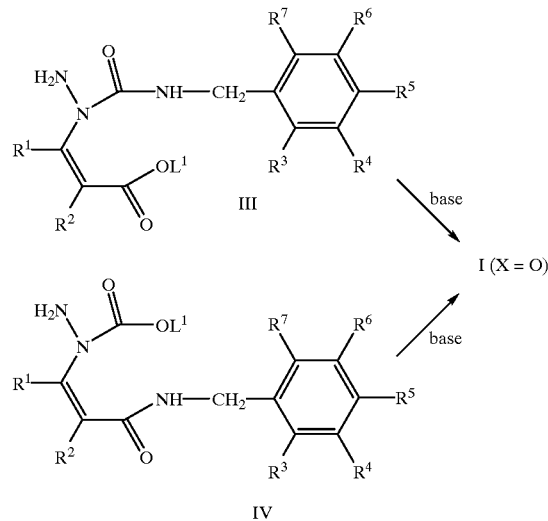

$L^1$ is low-molecular-weight alkyl, preferably $C_1$–$C_6$-alkyl, or phenyl.

As a rule, the cyclization is carried out in an inert organic solvent or diluent which is aprotic, for example in an aliphatic or cyclic ether, such as 1,2-dimethoxyethane, tetrahydrofuran and dioxane, in an aromatic substance, such as benzene and toluene, or in a polar solvent, such as dimethylformamide and dimethyl sulfoxide. Mixtures of polar solvents and a hydrocarbon, such as n-hexane, are also suitable. Depending on the starting compound, water may also act as the diluent.

Suitable bases are, preferably, alkali metal alcoholates, in particular the sodium alcoholates, alkali metal hydroxides, in particular sodium and potassium hydroxide, alkali metal carbonates, in Darticular sodium and potassium carbonate, and metal hydrides, in particular sodium hydride. When using sodium hydride as the base, it has proved advantageous to carry out the process in an aliphatic or cyclic ether, in dimethylformamide or in dimethyl sulfoxide.

In general 0.5 times to twice the molar amount of base based on the amount of III or IV is sufficient to carry out the reaction successfully.

As a rule, the reaction temperature is between (78)° C. and the boiling point of the reaction mixture in question, in particular at from (−60) to 60° C.

The process product is generally obtained as a metal salt, the metal corresponding to the cation of the base used. The salt can be isolated and purified in a manner known per se or, if desired, converted into the free compound III by means of an acid.

B) Sulfurization of a 1-amino-3-benzyluracil of the Formula I where X=oxygen:

$$I (X = O) \xrightarrow{\text{sulfurization}} I (X = S)$$

As a rule, the sulfurization is carried out in an inert solvent or diluent, for example in an aromatic hydrocarbon such as toluene and the xylenes, in an ether, such as diethyl ether, 1,2-dimethoxyethane and tetrahydrofuran, or in an organic amine, such as pyridine.

A particularly suitable sulfurization reagent is phosphorus (V) sulfide and 2,4-bis(4-methoxyphenyl)-1,3,2,4-dithiadiphosphetane-2,4-dithione ("Lawesson reagent").

In general, 1 to 5 times the molar amount based on the starting compound to be sulfurized is sufficient for a largely complete reaction.

The reaction temperature is normally at from 20 to 200° C., preferably at from 40° C. to the boiling point of the reaction mixture.

Process C)

Reaction of a 1H-3-phenyluracil of the formula V with an electrophilic aminating reagent in the presence of a base:

An aminating reagent which has proved suitable to date is 2,4-dinitrophenoxyamine, but hydroxylamine-O-sulfonic acid (HOSA), which has already been disclosed in the literature as aminating reagent (cf., for example, E. Hofer et al., Synthesis 1983, 466; W. Friedrichsen et al., Heterocycles 20 (1983) 1271; H. Hart et al., Tetrahedron Lett. 25 (1984) 2073; B. Vercek et al., Monatsh. Chem. 114 (1983) 789; G. Sosnousky et al., Z. Naturforsch. 38 (1983) 884; R. S. Atkinson et al., J. Chem. Soc. Perkin Trans. 1987, 2787), may, for example, also be used.

The amination can be carried out in a manner known per se (see, for example, T. Sheradsky, Tetrahedron Lett. 1968, 1909, M. P. Wentland et al., J. Med. Chem. 27 (1984) 1103 and, in particular, EP-A 240 194, EP-A 476 697 and EP-A 517 181, which teach the amination of uracils).

Examples of suitable bases are alkali metal alcoholates, such as sodium methylate and potassium tert-butanolate, alkali metal carbonates, such as sodium and potassium carbonate, or alkali metal hydrides, such as sodium hydride and potassium hydride.

In general, the reaction is carried out in a polar solvent, e.g. in dimethylformamide, N-methylpyrrolidone, in a sulfoxide, such as dimethyl sulfoxide, or in a carboxylic ester, such as ethyl acetate, which has proved particularly suitable to date.

Base and aminating agent preferably amount to 0.5 to twice the molar amount, based on the amount of III.

In general, the process is carried out at from (−10)° C. to the boiling point of the reaction mixture, in particular at from 10 to 70° C.

The 1H-3-phenyluracils V, in turn, can be obtained, for example, by cyclizing enamino esters VI or enamine carboxylates VII:

The information given under A) regarding the solvents/diluents, bases, amounts and the rection temperature also apply here.

If desired, the process product V where X=oxygen can be converted in accordance with process B) to give V where X=sulfur.

Process D)

Reaction of a 1-amino-6-haloalkyluracil VIII with a benzyl halide IX in the presence of a base:

Hal is halogen, particularly preferably bromine.

Examples of suitable bases are alkali metal alcoholates, such as sodium methylate, alkali metal carbonates, such as sodium and potassium carbonate, or alkali metal hydrides, such as sodium and potassium hydride.

It is also possible first to use a base to convert VIII into the alkali metal salt and subsequently to react the latter with IX.

In general, the process is carried out in an inert polar solvent or diluent, e.g. in dimethylformamide, N-methylpyrrolidone, in a sulfoxide, such as dimethyl sulfoxide, in a carboxylic ester, such as ethyl acetate, or in a ketone, such as acetone.

In general, the reaction temperature is from 0° C. to the boiling point of the reaction mixture.

The enamino esters of the formula III are novel. They, and the enamino esters VI, can be prepared by methods known per se, for example by one of the following processes:

E) Reaction of a 3-amino-4,4,4-trifluorobut-2-enoic ester X with a benzyl isocyanate XI in the presence of a base:

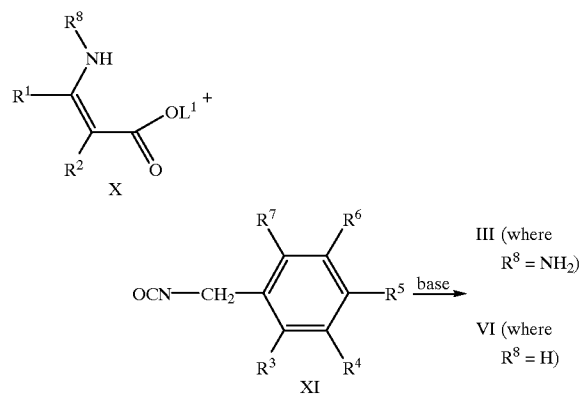

$R^8$ is hydrogen or amino.

A 3-amino-4,4,4-trifluorobut-2-enoic ester IX which has proved particularly suitable to date is the ethyl ester, but any other ester, preferably the alkyl esters, can also be used.

The reaction is expediently carried out in the presence of an essentially anhydrous aprotic organic solvent or diluent, for example an aliphatic or cyclic ether, such as diethyl ether, 1,2-dimethoxyethane, tetrahydrofuran and dioxane, an aliphatic or aromatic hydrocarbon, such as n-hexane, benzene, toluene and the xylenes, a halogenated, aliphatic hydrocarbon, such as methylene chloride, chloroform, carbon tetrachloride, 1,2-dichloroethane and chlorobenzene, an aprotic, polar solvent, such as dimethylformamide, hexamethylphosphoric triamide and dimethyl sulfoxide, or a mixture of these.

If desired, the process can also be carried out in the presence of a metal hydride base, such as sodium hydride and potassium hydride, an alkali metal alcoholate or alkaline earth metal alcoholate, such as sodium methanolate, sodium ethanolate and potassium tert-butanolate, or an organic tertiary base, such as triethylamine and pyridine, it being possible for the organic base to act simultaneously as the solvent.

It is expedient to employ the starting compounds in stoichiometric amounts, or else the process is carried out using a slight excess of one or the other reactant of up to 10 mol %. If the process is carried out in the absence of a solvent and in the presence of an organic base, it is recommended to employ the latter in a substantial excess.

In general, a reaction temperature of from (−80) to 50° C., in particular from (−60) to 30° C., will suffice.

In a particularly preferred embodiment, the resulting enamino ester is converted directly (i.e. "in situ") with excess base to give the corresponding end product I or V, which can then be purified by customary separation methods, such as crystallization and chromatography.

F) Reaction of a β-keto ester XII with a benzylurea XIII

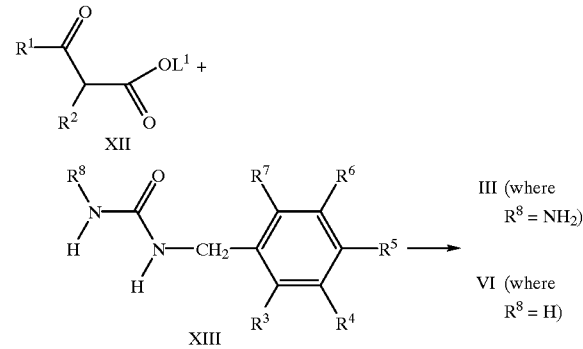

Preferably, the process is carried out under essentially anhydrous conditions in an inert solvent or diluent, particularly preferably in the presence of an acidic or basic catalyst.

Suitable solvents or diluents are, in particular, organic solvents which given an azeotropic mixture with water, for example aromatics, such as benzene, toluene and the xylenes, halogenated hydrocarbons, such as methylene chloride, chloroform, carbon tetrachloride and chlorobenzene, aliphatic and cyclic ethers, such as 1,2-dimethoxyethane, tetrahydrofuran and dioxane, or cyclohexane, but also alcohols, such as methanol and ethanol.

Suitable as acidic catalysts are, preferably, strong mineral acids, such as sulfuric acid and hydrochloric acid, phosphorus acids, such as orthophosphsoric acid and polyphosphoric acid, organic acids, such as p-toluenesulfonic acid, and acidic cation exchangers, such as "Amberlyst 15" (by Fluka).

Suitable basic catalyts are, for example, metal hydrides, such as sodium hydride, and, particularly preferably, metal alcoholates, such as sodium methanolate and sodium ethanolate.

It is expedient to react the β-keto ester XII and the benzylurea XIII in approximately stoichiometric amounts, or else the process is carried out with a slight excess of one or the other reactants of up to approximately 10 mol %.

In general, it suffices to employ half to twice the molar amount of catalyst based on the amount of one of the starting compounds.

In general, the reaction is carried out at from 60 to 120° C., in order rapidly to remove water which forms, preferably at the boiling point of the reaction mixture.

G)

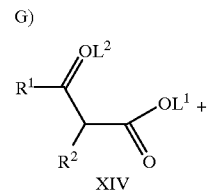

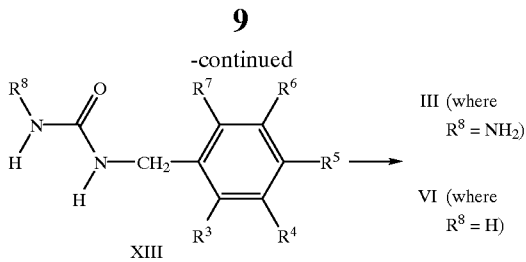

$L^2$ is $C_1$–$C_6$-alkyl or phenyl.

This reaction can be carried out in an inert organic solvent which is miscible with water, for example an aliphatic or cyclic ether, such as 1,2-dimethoxyethane, tetrahydrofuran and dioxane, or a lower alcohol, in particular ethanol, the reaction temperature generally being at from 50 to 100° C., preferably at the boiling temperature of the reaction mixture.

However, the reaction can also be carried out in an aromatic diluent, such as benzene, toluene and the xylenes, in which case an addition of either an acidic catalyst, such as hydrochloric acid and p-toluenesulfonic acid, or of a base, e.g. an alkali metal alcoholate, such as sodium methanolate and sodium ethanolate, is to be recommended. In this process variant, again, the reaction temperature is generally at from 50 to 100° C., but preferably from 60 to 80° C.

The information given for method $F_)$ regarding the amounts also applies here.

The enamine carboxylates of the formula IV are also novel; they—and the enamine carboxylates VII—can again be prepared in a manner known per se, for example from a benzylamine of the formula XIV in accordance with the following general equation $H_)$:

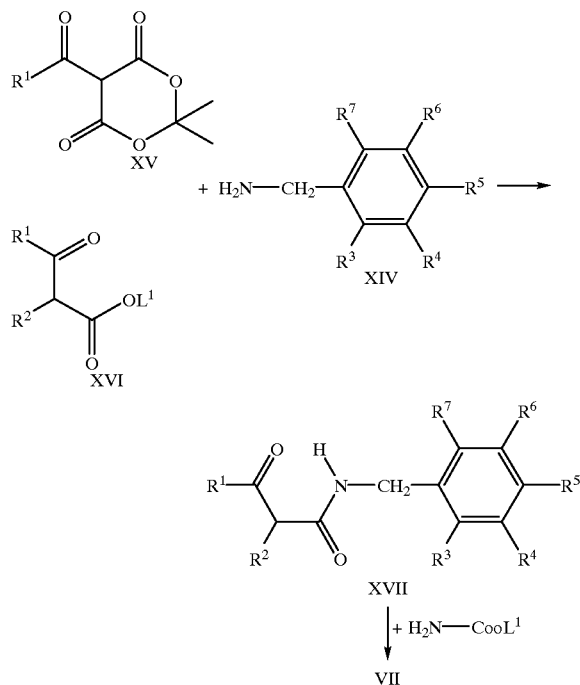

The reaction of XV with XIV is preferably carried out in an anhydrous inert aprotic solvent, for example in a halogenated hydrocarbon, such as methylene chloride, chloroform, carbon tetrachloride and chlorobenzene, an aromatic hydrocarbon, such as benzene, toluene and the xylenes, or an aliphatic or cyclic ether, such as diethyl ether, dibutyl ether, 1,2-dimethoxyethane, tetrahydrofuran and dioxane.

In this reaction (of XV with XIV), the reaction temperature is generally at from approximately 70 to 140° C., in particular at from 100 to 120° C.

The reaction of XVI with XIV is an aminolysis which is generally carried out either in the absence of a solvent [cf., for example, J. Soc. Dyes Col. 42, 81 (1926), Ber. 64, 970 (1931); Org. Synth., Coll. Vol. IV, 80 (1963) and J. Am. Chem. Soc. 70, 2402 (1948)] or in an inert anhydrous solvent/diluent, in particular in an aprotic solvent, for example in an aromatic substance, such as toluene and the xylenes, or a halogenated aromatic, such as chlorobenzene.

It is recommended to carry out the process in the presence of a basic catalyst, for example a higher-boiling amine [see, for example, Helv. Chim. Acta 11, 779 (1928) and U.S. Pat. No. 2,416,738] or of pyridine.

The reaction temperature is preferably at from approximately 20 to 160° C., in particular at from 80° C. to the boiling point of the reaction mixture or of the basic catalyst.

It is expedient to react the starting compounds in each case in approximately stoichiometric amounts, or else the process is carried out with a slight excess of one or the other reactants of up to approximately 10 mol %. If the process is carried out in the presence of a basic catalyst, the latter is usually employed in half to twice the molar amount based on the amount of one of the educts.

The subsequent reaction of the resulting compounds of the formula XVII with the amine $H_2N$-$CooL^1$ is advantageously carried out in a largely anhydrous solvent/diluent under atmospheric pressure, particularly preferably in the presence of an acidic catalyst.

Suitable solvents/diluents are, in particular, organic liquids which can be mixed with water to give an azeotropic mixture, for example aromatics, such as benzene, toluene and the xylenes, or halogenated hydrocarbons, such as carbon tetrachloride and chlorobenzene.

Suitable catalysts are, in particular, strong mineral acids, such as sulfuric acid, organic acids, such as p-toluenesulfonic acid, phopshorus acids, such as orthophosphoric acid and polyphosphoric acid, or acidic cation exchangers, such as "Amberlyst 15" (by Fluka).

In general, the reaction temperature is at from approximately 70 to 150° C.; in order rapidly to remove the water of reaction, however, the process is expediently carried out at the boiling point of the reaction mixture in question.

Unless otherwise specified, all processes described above are expediently carried out under atmospheric pressure or under the inherent pressure of the reaction mixture in question.

As a rule, the reaction mixtures are worked up in a manner known per se, e.g. by removing the solvent, partitioning the residue in a mixture of water and a suitable organic solvent, and working up the organic phase to give the product.

The 1-amino-3-benzyluracils I can be obtained, upon their preparation, as mixtures of isomers, but, if desired, they can be separated by the methods customary for this purpose, such as crystallization or chromatography, also on an optically active absorbate, to give the pure isomers. Pure optically active isomers can be prepared advantageously from suitable optically active starting materials.

Agriculturally useful salts of the compounds I can be formed by reaction with a base of the cation in question, preferably an alkali metal hydroxide or alkali metal hydride, or by reaction with an acid of the anion in question, preferably of hydrochloric acid, hydrobromic acid, sulfuric acid, phosphoric acid or nitric acid.

Salts of I whose metal ion is not an alkali metal ion can also be prepared in the customary manner by double decomposition of the alkali metal salt in question, and ammonium, phosphonium, sulfonium and sulfoxonium salts by means of ammonia, phosphonium hydroxide, sulfonium hydroxide or sulfoxonium hydroxide.

The compounds I and their agriculturally useful salts—as mixtures of isomers and also in the form of the pure isomers—are suitable for use as herbicides. They are capable of effecting very efficient control of broad-leaved weeds and grass weeds in crops such as wheat, rice, maize, soya and cotton without harming the crop plants to a significant extent. This effect is particularly pronounced at low rates of application.

Depending on the method of application in question, the compounds I, or herbicidal compositions comprising them, can also be employed in a further number of crop plants for eliminating undesirable plants. The following are examples of suitable crops: *Allium cepa, Ananas comosus, Arachis hypogaea, Asparagus officinalis, Beta vulgaris* ssp. *altissima, Beta vulgaris* ssp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spp., *Manihot esculenta, Medicago sativa,* Musa spp., *Nicotiana tabacum* (*N.rustica*), *Olea europaea, Oryza sativa, Phaseolus lunatus, Phaseolus vulgaris, Picea abies,* Pinus spp., *Pisum sativum, Prunus avium, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera* and *Zea mays*.

Moreover, the compounds I can be employed in crops which have been rendered largely resistant to the action of I by means of breeding and/or genetic engineering methods.

Furthermore, the 1-amino-3-benzyluracils I are also suitable for the desiccation and/or defoliation of plants.

As desiccants, they are particularly suitable for desiccating the aerial parts of crop plants such as potatoes, oilseed rape, sunflowers and soya beans. This allows completely mechanical harvesting of these important crop plants.

It is also of economic interest to facilitate harvesting, which is made possible by concentrating, over a period of time, dehiscence, or reducing the adherence to the tree, in citrus fruits, olives or other species and varieties of pomaceous fruit, stone fruit and hard-shelled fruit. The same mechanism, i.e. promotion of the formation of abscission tissue between fruit or leaf and shoot of the plants is also important for readily controllable defoliation of useful plants, in particular cotton.

Moreover, shortening the period within which the individual cotton plants mature results in an improved fiber quality after harvesting.

The compounds I, or the herbicidal compositions comprising them, can be used, for example, in the form of ready-to-spray aqueous solutions, powders, suspensions, also high-percentage aqueous, oily or other suspensions or dispersions, emulsions, oil dispersions, pastes, dusts, materials for spreading or granules, by means of spraying, atomizing, dusting, spreading or pouring. The use forms depend on the intended aims; in any case, they should guarantee the finest possible distribution of the active ingredients according to the invention.

Suitable inert auxiliaries are essentially: mineral oil fractions of medium to high boiling point, such as kerosine and diesel oil, furthermore coal tar oils and oils of vegetable or animal origin, aliphatic, cyclic and aromatic hyrocarbons, e.g. paraffins, tetrahydronaphthalene, alkylated naphthalenes and their derivatives, alkylated benzenes and their derivatives, alcohols, such as methanol, ethanol, propanol, butanol and cyclohexanol, ketones, such as cyclohexanone, strongly polar solvents, e.g. amines, such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the substances, either as such or dissolved in an oil or solvent, can be homogenized in water by means of a wetting agent, tackifier, dispersant or emulsifier. Alternatively, it is possible to prepare concentrates comprising active ingredient, wetting agent, tackifier, dispersant or emulsifier and, if desired, solvent or oil, which are suitable for dilution with water.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isoctyl-, octyl- or nonylphenol, alkylphenyl polyglycol ether, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for spreading and dusts can be prepared by mixing or grinding the active ingredients together with a solid carrier.

Granules, e.g. coated granules, impregnated granules and homogeneous granules, can be prepared by binding the active ingredients to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers, such as ammonium sulfate, ammonium phosphate, ammonium nitrate, ureas, and products of vegetable origin, such as cereal meal, tree bark meal, wood meal and nutshell meal, cellulose powders, or other solid carriers.

The concentrations of the active ingredients I in the ready-to-use products can be varied within wide ranges, such as from 0.01 to 95% by weight, preferably 0.5 to 90% by weight. The active ingredients are employed in a purity of 90% to 100%, preferably 95% to 100% (according to NMR spectrum).

The following formulation examples illustrate the preparation of such products:

I. 20 parts by weight of compound No. 1 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

II. 20 parts by weight of compound No. 1 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

III. 20 parts by weight of active ingredient No. 1 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

IV. 20 parts by weight of active ingredient No. 1 are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture comprising 0.1% by weight of the active ingredient.

V. 3 parts by weight of active ingredient No. 1 are mixed with 97 parts by weight of finely divided kaolin. This gives a dust comprising 3% by weight of the active ingredient.

VI. 20 parts by weight of active ingredient No. 1 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

The active ingredients I or the herbicidal compositions can be applied pre- or postemergence. If the active ingredients are less well tolerated by certain crop plants, application techniques may be used in which the herbicidal compositions are sprayed, with the aid of the spraying equipment, in such a way that they come into contact as little as possible, if at all, with the leaves of the sensitive crop plants, while the active ingredients reach the leaves of undesirable plants growing underneath, or the naked soil surface (post-directed, lay-by).

The application rates of active ingredient I are from 0.001 to 3.0, preferably 0.01 to 1.0, kg of active ingredient (a.i.) per ha, depending on the control target, the season, the target plants and the growth stage.

To widen the spectrum of action and to achieve synergistic effects, the 1-amino-3-benzyluracils I may be mixed with a large number of representatives of other groups of herbicidal or growth-regulating active ingredients and then applied concomitantly. Suitable components for mixtures are, for example, diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives which have attached to them in the 2-position, for example, a carboxyl or carbimino group, quinolinecarboxylic acid derivatives, imidazolinones, sulfonamides, sulfonylureas, aryloxy- or heteroaryloxyphenoxypropionic acids and their salts, esters and amides, and others.

Furthermore, it may be advantageous to apply the compounds I, alone or in combination with other herbicides, together with further crop protection agents, for example with pesticides or agents for controlling phytopathogenic fungi or bacteria. Also of interest is the miscibility with mineral salt solutions which are employed for treating nutrient and trace element deficiencies. Non-phytotoxic oils and oil concentrates may also be added.

Preparation Example 3-(2,3-Dichlorobenzyl)-2,4-dioxo-1-amino-6-trifluoromethyl-1,2,3,4-tetrahydropyrimidine

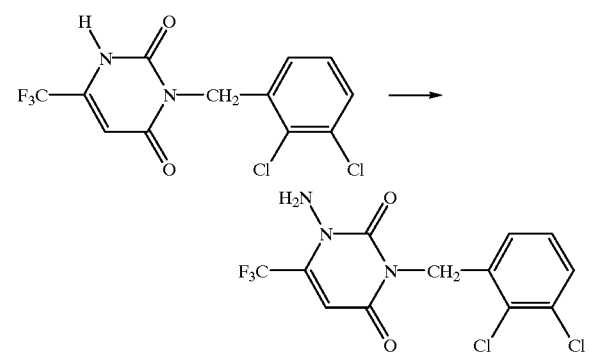

A solution of 0.0058 mol of 3-(2,3-dichlorobenzyl)-2,4-dioxo-1-H-6-trifluoromethyl-1,2,3,4-tetrahydropyrimidine in 30 ml of ethyl acetate was treated with 0.011 mol of potassium carbonate and then 0.0062 mol of 2,4-dinitrophenoxyamine. The reaction solution was subsequently stirred for 8 hours at 60° C., whereupon the resulting solids were separated off and washed with diisopropyl ether. The filtrate was washed twice with water, then dried over sodium sulfate and finally concentrated. The residue was taken up in 30 ml of diethyl ether. The end product was precipitated by adding petroleum ether. Yield: 0.6 g.

Preparation of the precursor 3-(2,3-dichlorobenzyl)-2,4-dioxo-1-H-6-trifluoromethyl-1,2,3,4-tetrahydropyrimidine

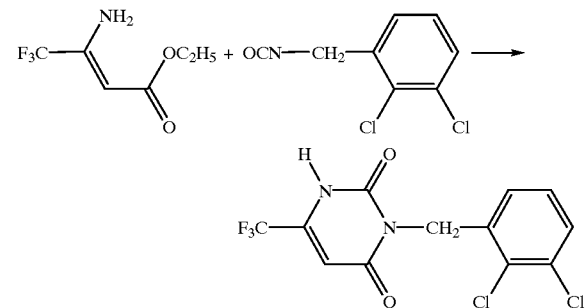

0.03 mol of ethyl 3-amino-4,4,4-trifluorobut-2-enoate were added dropwise at 0° C. to 0.03 mol of sodium hydride in 60 ml of dimethylformamide. The mixture was subsequently stirred for a further 30 minutes at this temperature. The reaction solution was then cooled to (−10)° C., and 0.03 mol of 2,3-dichlorobenzyl isocyanate, dissolved in 5 ml of dimethylformamide, were added dropwise. The reaction solution was subsequently heated slowly to room temperature and stirred for a further 12 hours. Then, the mixture was stirred for a further 2 hours at 80° C. before most of the solvent was removed. The resulting solids were separated off by adding 100 ml of water. The filtrate was washed twice using in each case 50 ml of toluene. After the aqueous phase had been acidified with dilute hydrochloric acid, the product was extracted twice using in each case 100 ml of methylene chloride. The organic phases were washed with water, then dried over sodium sulfate and finally concentrated. The product was precipitated from the residue by adding petroleum ether. Yield: 6 g.

Preparation of 2,3-dichlorobenzyl isocyanate:

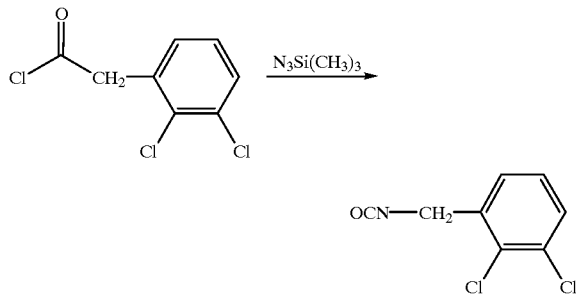

0.071 mol of triethylsilane were slowly added dropwise to a mixture, which had been heated to room temperature, of 0.065 mol of 2,3-dichlorobenzoyl chloride, 1.5 ml of triethylamine and 100 ml of toluene. The mixture was subsequently stirred for a further 30 minutes at this temperature. After the solvent had been removed, an oil was obtained. Yield: 13 g.

In addition to the compound described above, further 1-amino-3-benzyluracils I which were prepared, or can be prepared, in a similar manner are listed in the table which follows:

TABLE I

![structure with H2N, F3C, N-CH2-aryl with R1, R2, R3]

($R^4$, $R^5$ = H)

| No. | $R^1$ | $R^2$ | $R^3$ | M.p./$^1$H NMR [ppm]/MS [mz] |
|-----|-------|-------|-------|------------------------------|
| 1 | Cl | Cl | H | 157–158° C. |
| 2 | Cl | Cl | $OCH_3$ | |
| 3 | Cl | Cl | $OC_2H_5$ | |
| 4 | Cl | Cl | $OCH(CH_3)_2$ | |

Use Examples (herbicidal activity)

The herbicidal action of the 1-amino-3-benzyluracils I was demonstrated by the following greenhouse experiments:

The culture containers used were plastic flower pots containing loamy soil with approximately 3.0% of humus as the substrate. The seeds of the test plants were sown separately for each species.

In the case of the preemergence treatment, the active ingredients, which had been suspended or emulsified in water, were applied directly after sowing by means of finely distributing nozzles. The containers were irrigated slightly to promote germination and growth and subsequently covered with translucent plastic hoods until the plants had rooted. This cover causes uniform germination of the test plants, unless this was adversely affected by the active ingredients.

For the postemergence treatment, the test plants were first grown to a plant height of 3 to 15 cm, depending on the plant habit, and only then treated with the active ingredients which had been suspended or emulsified in water. For this purpose, the test plants were either sown directly and grown in the same containers, or they were first grown separately as seedlings and then transplanted into the test containers a few days prior to treatment. The rate of application for the postemergence treatment was 0.0312 or 0.0156 kg of a.i. (active ingredient) per ha.

Depending on the species, the plants were kept at from 10 to 25° C. or 20 to 35° C. The test period extended over 2 to 4 weeks. During this time, the plants were tended and their response to the individual treatments was evaluated.

The test was evaluated using a scale from 0 to 100. 100 means no emergence of the plants or complete destruction of at least the aerial parts, and 0 means no damage or normal course of growth.

The plants used in the greenhouse experiments belonged to the following species:

| Scientific Name | Common Name |
|-----------------|-------------|
| *Abutilon theophrasti* | velvet leaf |
| *Amaranthus retroflexus* | redroot pigweed |
| *Galium aparine* | catchweed bedstraw |
| *Ipomoea* subspecies | morningglory |

At a rate of application of 0.0312 or 0.0156 kg of a.i./ha, applied postemergence, compound No. 1 showed a very good herbicidal action against the abovementioned plants.

Use Examples (desiccant/defoliant activity)

The test plants used were young cotton plants with 4 leaves (without cotyledons) which were grown under greenhouse conditions (relative atmospheric humidity 50 to 70%; day/night temperature 27/20° C.).

The young cotton plants were subjected to foliar treatment to drip point with aqueous preparations of the active ingredients (with an addition of 0.15% by weight of the fatty alcohol alkoxylate Plurafac LF 700, based on the spray mixture). The amount of water applied was 1000 l/ha (converted). After 13 days, the number of shed leaves and the degree of defoliation in % were determined.

No leaves were shed amongst the untreated control plants.

What is claimed is:

1. A 1-amino-3-benzyluracil of the formula I

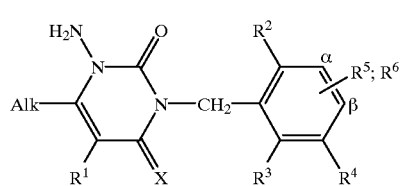

where the variables have the following meanings:

X is oxygen or sulfur;

Alk is $C_1$–$C_4$-haloalkyl;

$R^1$ is hydrogen or halogen;

$R^2$ and $R^3$ independently of one another are hydrogen, cyano, thiocyanato, halogen, $C_1$–$C_4$-haloalkyl, $C_1$–$C_4$-haloalkoxy or $C_1$–$C_4$-haloalkylthio;

$R^4$ is hydrogen, cyano, thiocyanato, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-haloalkylthio or $C_1$–$C_6$-alkylamino-carbonyl;

R⁵ in the α or β position is hydrogen, cyano, nitro, hydroxyl, amino, halogen, $C_1$–$C_4$-alkylamino which is unsubstituted or substituted by $C_1$–$C_4$-alkyl, ($C_1$–$C_4$-alkyl)carbonyl or ($C_1$–$C_4$-alkoxy)carbonyl, $C_1$–$C_6$-haloalkoxy, $C_1$–$C_6$-haloalkylthio, $C_1$–$C_6$-alkoxy, $C_1$–$C_6$-alkylthio, $C_3$–$C_6$-cycloalkoxy, $C_3$–$C_6$-cycloalkylthio, $C_3$–$C_6$-alkenyloxy, $C_3$–$C_6$-alkenylthio, $C_3$–$C_6$-alkynyloxy, $C_3$–$C_6$-alkynylthio, ($C_1$–$C_6$-alkyl)carbonyloxy, ($C_1$–$C_6$-alkyl)carbonylthio, ($C_3$–$C_6$-alkenyl)carbonyloxy, ($C_3$–$C_6$-alkenyl)carbonylthio, ($C_3$–$C_6$-alkynyl)carbonyloxy, ($C_3$–$C_6$-alkynyl)carbonylthio, $C_1$–$C_6$-alkyl-sulfonyloxy or $C_1$–$C_6$-alkylsulfonyl, where the last mentioned 16 radicals are unsubstituted or carry one to three substituents selected from the group consisting of
  halogen, nitro, cyano, hydroxy, $C_3$–$C_6$-cycloalkyl, $C_1$–$C_6$-alkoxy, $C_3$–$C_6$-cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, $C_1$–$C_6$-alkylsulfinyl, $C_1$–$C_6$-alkylsulfonyl, $C_1$–$C_6$-alkylideneaminoxy,
  phenyl, phenoxy and phenylsulfonyl which are unsubstituted or carry one to three substituents selected from the group consisting of halogen, nitro, cyano, $C_1$–$C_6$-alkyl, $C_1$–$C_6$-alkoxy and $C_1$–$C_6$-haloalkyl, —CO—R⁷, —COOR⁷, —COSR⁷, —CON(R⁷)R⁸, —OCO—R⁷, —OCOOR⁷, —OCOSR⁷, —OCON(R⁷)R⁸ and —N(R⁷)R⁸, R⁶ in the α position, in which case R⁵ is in the β position, or in the β position, in which case R⁵ is in the α position, is hydrogen, hydroxyl, mercapto, halogen, $C_1$–$C_6$-haloalkoxy, $C_1$–$C_6$-haloalkylthio, $C_1$–$C_6$-alkylthio-($C_1$–$C_6$-alkyl)carbonyl, ($C_1$–$C_6$-alkyl)iminooxycarbonyl, $C_1$–$C_6$-alkoxy, $C_1$–$C_6$-alkylthio, $C_3$–$C_6$-cycloalkoxy, $C_3$–$C_6$-cycloalkylthio, $C_2$–$C_6$-alkenyloxy, $C_2$–$C_6$-alkenylthio, $C_2$–$C_6$-alkynyloxy, $C_2$–$C_6$-alkynylthio, ($C_1$–$C_6$-alkyl)carbonyloxy, ($C_1$–$C_6$-alkyl)carbonylthio, ($C_1$–$C_6$-alkoxy)carbonyloxy, ($C_2$–$C_6$-alkenyl)carbonyloxy, ($C_2$–$C_6$-alkenyl)carbonylthio, ($C_2$–$C_6$-alkynyl)carbonyloxy, ($C_2$–$C_6$-alkynyl)carbonylthio, $C_1$–$C_6$-alkylsulfonyloxy or $C_1$–$C_6$-alkylsulfonyl, where each of the last-mentioned 17 radicals is unsubstituted or carries one to three substituents selected from the group consisting of
  halogen, nitro, cyano, hydroxy, $C_3$–$C_6$-cycloalkyl, $C_1$–$C_6$-alkoxy, $C_3$–$C_6$-cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, $C_1$–$C_6$-alkylsulfinyl, $C_1$–$C_6$-alkylsulfonyl, $C_1$–$C_6$-alkylideneaminoxy,
  phenyl, phenoxy and phenylsulfonyl which are unsubstituted or carry one to three substituents selected from the group consisting of halogen, nitro, cyano, $C_1$–$C_6$-alkyl, $C_1$–$C_6$-haloalkyl, $C_1$–$C_6$-alkoxy and ($C_1$–$C_6$-alkoxy)carbonyl,
  —CO—R⁹, —COOR⁹, —COSR⁹, —CON(R⁹)R¹⁰, —OCO—R⁹, —OCOOR⁹, —OCOSR⁹, —OCON(R⁹)R¹⁰ and —N(R⁹)R¹⁰, and
  the group —C(R²¹)=N—OR²⁰; —CY—R¹¹, —C(R¹¹)(Z¹R¹²)(Z²R¹³), —C(R¹¹)=C(R¹⁴)—CN, —C(R¹¹)=C(R¹⁴)—CO—R¹⁵, —CH(R¹¹)—CH(R¹⁴)—CO—R¹⁵, —C(R¹¹)=C(R¹⁴)—CH₂—CO—R¹⁵, —C(R¹¹)=C(R¹⁴)—C(R¹⁶)=C(R¹⁷)—CO—R¹⁵, —C(R¹¹)=C(R¹⁴)—CH₂—CH(R¹⁸)—CO—R¹⁵, —CO—OR¹⁹, —CO—SR¹⁹, —CO—N(R¹⁹)—OR²⁰, —C≡C—CO—N(R¹⁹)—OR²⁰, —C≡C—CS—N(Rl¹⁹)—OR²⁰, —C(R¹¹)=C(R¹⁴)—CO—N(R¹⁹)—OR²⁰, —C(R¹¹)=C(R¹⁴)—CS—N(R¹⁹)—OR²⁰, —C(R¹¹)=C(R¹⁴)—C(R²¹)=N—OR²⁰, —C(R²¹)=N—OR²⁰, —C≡C—C(R²¹)=N—OR²⁰, —C(Z¹R¹²)(Z²R¹³)—OR¹⁹, —C(Z¹R¹²)(Z²R¹³)—SR¹⁹, —C(Z¹R¹²)(Z²R¹³)—N(R²³)R²⁴, —N(R²³)R²⁴, —CON(R²³)R²⁴,

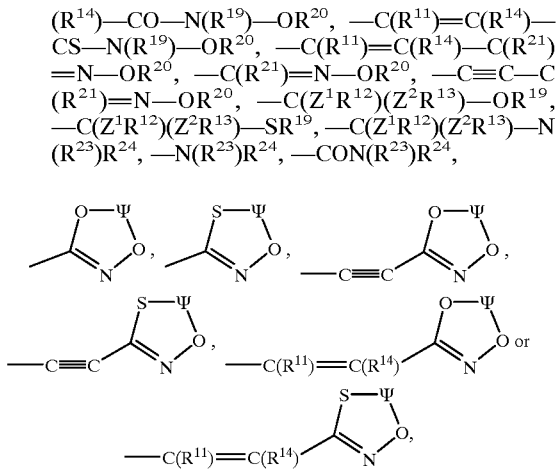

$Z^1$ and $Z^2$ are oxygen or sulfur,
Ψ is $C_1$–$C_3$-alkylene which is unsubstituted or carries a $C_1$–$C_6$-alkyl substituent;
R⁷ and R⁹ are hydrogen, $C_1$–$C_6$-alkyl, $C_3$–$C_6$-cycloalkyl, $C_3$–$C_6$-alkenyl, $C_3$–$C_6$-alkynyl, $C_1$–$C_6$-alkoxy-$C_1$–$C_6$-alkyl, ($C_1$–$C_6$-alkoxy)carbonyl-$C_1$–$C_6$-alkyl, ($C_3$–$C_6$-alkenyloxy)carbonyl-$C_1$–$C_6$-alkyl, phenyl or phenyl-$C_1$–$C_6$-alkyl, where the phenyl group and the phenyl ring of the phenyl alkyl group is unsubstituted or carries one to three radicals selected from the group consisting of halogen, nitro, cyano, $C_1$–$C_6$-alkyl, $C_1$–$C_6$-haloalkyl, $C_1$–$C_6$-alkoxy and ($C_1$–$C_6$-alkyl)carbonyl
R⁸ and R¹⁰ are hydrogen, hydroxyl, $C_1$–$C_6$-alkyl, $C_3$–$C_6$-cycloalkyl, $C_1$–$C_6$-alkoxy, ($C_1$–$C_6$-alkoxy)carbonyl-$C_1$–$C_6$-alkoxy, $C_3$–$C_6$-alkenyl or $C_3$–$C_6$-alkenyloxy
R¹¹ is hydrogen, cyano, $C_1$–$C_6$-alkyl, $C_1$–$C_6$-haloalkyl, $C_2$–$C_6$-alkenyl, $C_2$–$C_6$-alkynyl $C_3$–$C_6$-cycloalkyl, $C_1$–$C_6$-alkoxy-$C_1$–$C_6$-alkyl or ($C_1$–$C_6$-alkoxy)carbonyl;
R¹² and R¹³ independently of one another are $C_1$–$C_6$-alkyl, $C_1$–$C_6$-haloalkyl, $C_3$–$C_6$-alkenyl, $C_3$–$C_6$-alkynyl, $C_1$–$C_6$-alkoxy-$C_1$–$C_6$-alkyl, or
R¹² and R¹³ together are a saturated or unsaturated, 2- to 4-membered carbon chain, which is unsubstituted or carries one to three radicals selected from the group consisting of cyano, nitro amino, halogen, $C_1$–$C_6$-alkyl, $C_2$–$C_6$-alkenyl, $C_1$–$C_6$-alkoxy, $C_2$–$C_6$-alkenyloxy $C_2$–$C_6$-alkynyloxy, $C_1$–$C_6$-haloalkyl, cyano-$C_1$–$C_6$-alkyl, hydroxy-$C_1$–$C_6$-alkyl, $C_1$–$C_6$-alkoxy-$C_1$–$C_6$-alkyl, $C_3$–$C_6$-alkenyloxy-$C_1$–$C_6$-alkyl, $C_3$–$C_6$-alkynyloxy-$C_1$–$C_6$-alkyl, $C_3$–$C_6$-cycloalkyl, $C_3$–$C_6$-cycloalkoxy, carboxyl, ($C_1$–$C_6$-alkoxy)carbonyl, ($C_1$–$C_6$-alkyl)carbonyloxy-$C_1$–$C_6$-alkyl and phenyl which is unsubstituted or carries one to three substituents selected from the group consisting of cyano, nitro, amino, halogen, $C_1$–$C_6$-alkyl, $C_1$–$C_6$-haloalkyl, $C_1$–$C_6$-alkoxy and ($C_1$–$C_6$-alkoxy)carbonyl, and where the carbon chain can also carry an oxo group, a fused or spiro-linked 3- to 7-membered carbon ring which is unsubstituted or carries one or two of the following substituents: cyano, $C_1$–$C_6$-alkyl, $C_2$–$C_6$-alkenyl, $C_1$–$C_6$-alkoxy, cyano-$C_1$–$C_6$-alkyl, $C_1$–$C_6$-haloalkyl and ($C_1$–$C_6$-alkoxy)carbonyl;
R¹⁴ is hydrogen, cyano, halogen, $C_1$–$C_6$-alkyl, $C_1$–$C_6$-haloalkyl, $C_1$–$C_6$-alkoxy, ($C_1$–$C_6$-alkyl)carbonyl or ($C_1$–$C_6$-alkoxy)carbonyl;

$R^{15}$ is hydrogen, O—$R^{22}$, S—$R^{22}$, $C_1$–$C_6$-alkyl which is unsubstituted or carries one or two $C_1$–$C_6$-alkoxy substituents, or is $C_2$–$C_6$-alkenyl, $C_2$–$C_6$-alkynyl, $C_1$–$C_6$-haloalkyl, $C_3$–$C_6$-cycloalkyl, $C_1$–$C_6$-alkylthio-$C_1$–$C_6$-alkyl, $C_1$–$C_6$-alkyliminooxy, —N($R^{23}$)$R^{24}$ or phenyl which is unsubstituted or carries one to three substituents selected from the group consisting of cyano, nitro, halogen, $C_1$–$C_6$-alkyl, $C_2$–$C_6$-alkenyl, $C_1$–$C_6$-haloalkyl, $C_1$–$C_6$-alkoxy and ($C_1$–$C_6$-alkoxy)carbonyl, $R^{16}$ is hydrogen, cyano, halogen, $C_1$–$C_6$-alkyl, $C_3$–$C_6$-alkenyl, $C_3$–$C_6$-alkynyl, $C_1$–$C_6$-alkoxy-$C_1$–$C_6$-alkyl, ($C_1$–$C_6$-alkyl)carbonyl, ($C_1$–$C_6$-alkoxy)carbonyl, —N($R^{25}$)$R^{26}$, or is phenyl which is unsubstituted or carries one to three substituents selected from the group consisting of cyano, nitro, halogen, $C_1$–$C_6$-alkyl, $C_1$–$C_6$-haloalkyl, $C_3$–$C_6$-alkenyl, $C_1$–$C_6$-alkoxy and ($C_1$–$C_6$-alkoxy)carbonyl;

$R^{17}$ is hydrogen, cyano, halogen, $C_1$–$C_6$-alkyl, $C_1$–$C_6$-alkoxy, $C_1$–$C_6$-haloalkyl, ($C_1$–$C_6$-alkyl)carbonyl or ($C_1$–$C_6$-alkoxy)carbonyl;

$R^{18}$ is hydrogen, cyano, $C_1$–$C_6$-alkyl or ($C_1$–$C_6$-alkoxy)carbonyl;

$R^{19}$ is hydrogen, $C_1$–$C_6$-alkyl, $C_1$–$C_6$-haloalkyl, $C_2$–$C_6$-alkenyl or $C_2$–$C_6$-alkynyl, where each of the last mentioned 4 groups is unsubstituted or carries one or two of the following radicals: cyano, halogen, hydroxyl, hydroxycarbonyl, $C_1$–$C_6$-alkoxy, $C_1$–$C_6$-alkylthio, ($C_1$–$C_6$-alkyl)carbonyl, ($C_1$–$C_6$-alkoxy)carbonyl, ($C_1$–$C_6$-alkyl)carbonyloxy, ($C_3$–$C_6$-alkenyloxy)carbonyl; or is ($C_1$–$C_6$-alkyl)carbonyl, ($C_1$–$C_6$-haloalkyl)carbonyl, ($C_1$–$C_6$-alkoxy)carbonyl, $C_1$–$C_6$-alkylaminocarbonyl, di($C_1$–$C_6$-alkyl)aminocarbonyl, $C_1$–$C_6$-alkyloximino-$C_1$–$C_6$-alkyl, $C_3$–$C_6$-cycloalkyl, phenyl or phenyl-$C_1$–$C_6$-alkyl, where the phenyl rings are unsubstituted or carry one to three substituents selected from the group consisting of cyano, nitro, halogen, $C_1$–$C_6$-alkyl, $C_1$–$C_6$-haloalkyl, $C_1$–$C_6$-alkoxy and ($C_1$–$C_6$-alkoxy)carbonyl;

$R^{20}$ is hydrogen, $C_1$–$C_6$-alkyl, $C_1$–$C_6$-haloalkyl, $C_3$–$C_6$-cycloalkyl, $C_3$–$C_6$-alkenyl, $C_3$–$C_6$-alkynyl, hydroxy-$C_1$–$C_6$-alkyl, $C_1$–$C_6$-alkoxy-$C_1$–$C_6$-alkyl, $C_1$–$C_6$-alkylthio-$C_1$–$C_6$-alkyl, cyano-$C_1$–$C_6$-alkyl, ($C_1$–$C_6$-alkyl)carbonyl-$C_1$–$C_6$-alkyl, ($C_1$–$C_6$-alkoxy)carbonyl-$C_1$–$C_6$-alkyl, ($C_1$–$C_6$-alkoxy)carbonyl-$C_2$–$C_6$-alkenyl, ($C_1$–$C_6$-alkyl)carbonyloxy-$C_1$–$C_6$-alkyl or phenyl-$C_1$–$C_6$-alkyl, where the phenyl ring is unsubstituted or carries one to three substituents selected from the group consisting of cyano, nitro, halogen, $C_1$–$C_6$-alkyl, $C_1$–$C_6$-haloalkyl, $C_1$–$C_6$-alkoxy and ($C_1$–$C_6$-alkoxy)carbonyl;

$R^{21}$ is hydrogen, halogen, $C_1$–$C_6$-alkyl, $C_1$–$C_6$-haloalkyl, $C_1$–$C_6$-alkoxy, $C_1$–$C_6$-haloalkoxy, $C_3$–$C_6$-alkenyloxy, $C_1$–$C_6$-alkylthio, $C_1$–$C_6$-haloalkylthio, ($C_1$–$C_6$-alkyl)carbonyloxy, ($C_1$–$C_6$-haloalkyl)carbonyloxy, $C_1$–$C_6$-alkylsulfonyloxy or $C_1$–$C_6$-haloalkylsulfonyloxy, where the last mentioned 11 radicals are unsubstituted or carry one of the following substituents: hydroxyl, cyano, hydroxycarbonyl, $C_1$–$C_6$-alkoxy, $C_1$–$C_6$-alkylthio, ($C_1$–$C_6$-alkyl)carbonyl, ($C_1$–$C_6$-alkoxy)carbonyl, ($C_1$–$C_6$-alkyl)aminocarbonyl, di($C_1$–$C_6$-alkyl)aminocarbonyl or ($C_1$–$C_6$-alkyl)carbonyloxy, ($C_1$–$C_6$-alkyl)carbonyl, ($C_1$–$C_6$-haloalkyl)carbonyl, ($C_1$–$C_6$-alkoxy)carbonyl, ($C_1$–$C_6$-alkoxy)carbonyloxy, ($C_1$–$C_6$-alkyl)carbonylthio, ($C_1$–$C_6$-haloalkyl)carbonylthio, ($C_1$–$C_6$-alkoxy)carbonylthio, $C_2$–$C_6$-alkenyl, $C_2$–$C_6$-alkenylthio, $C_3$–$C_6$-alkynyl, $C_3$–$C_6$-alkynyloxy, $C_3$–$C_6$-alkynylthio, ($C_2$–$C_6$-alkynyl)carbonyloxy, $C_3$–$C_6$-alkynylsulfonyloxy, $C_3$–$C_6$-cycloalkyl, $C_3$–$C_6$-cycloalkoxy, $C_3$–$C_6$-cycloalkylthio, ($C_3$–$C_6$-cycloalkyl)carbonyloxy, $C_3$–$C_6$-cycloalkylsulfonyloxy, phenyl, phenoxy, phenylthio, benzoyloxy, phenylsulfonyloxy, phenyl-$C_1$–$C_6$-alkyl, phenyl-$C_1$–$C_6$-alkoxy, phenyl-$C_1$–$C_6$-alkylthio, phenyl-($C_1$–$C_6$-alkyl)carbonyloxy or phenyl-($C_1$–$C_6$-alkyl)sulfonyloxy, where the phenyl rings of the last-mentioned 10 radicals are unsubstituted or carry one to three substituents selected from the group consisting of cyano, nitro, halogen, $C_1$–$C_6$-alkyl, $C_1$–$C_6$-haloalkyl, $C_1$–$C_6$-alkoxy and ($C_1$–$C_6$-alkoxy)carbonyl;

$R^{22}$ having one of the meanings of $R^{19}$;

$R^{23}$, $R^{24}$, $R^{25}$ and R26 independently of one another are hydrogen, $C_1$–$C_6$-alkyl, $C_2$–$C_6$-alkenyl, $C_2$–$C_6$-alkynyl, $C_3$–$C_6$-cycloalkyl, $C_1$–$C_6$-haloalkyl, $C_1$–$C_6$-alkoxy-$C_1$–$C_6$-alkyl, ($C_1$–$C_6$-alkyl)carbonyl, ($C_1$–$C_6$-alkoxy)carbonyl, ($C_1$–$C_6$-alkoxy)carbonyl-$C_1$–$C_6$-alkyl, ($C_1$–$C_6$-alkoxy)carbonyl -$C_2$–$C_6$-alkenyl, where the alkenyl chain is unsubstituted or carries one to three halogen and/or cyano radicals, or are $C_1$–$C_6$-alkylsulfonyl, ($C_1$–$C_6$-alkoxy)carbonyl-$C_1$–$C_6$-alkylsulfonyl, phenyl or phenylsulfonyl, where the two phenyl rings are unsubstituted or carry one to three substituents selected from the group consisting of cyano, nitro, halogen, $C_1$–$C_6$-alkyl, $C_1$–$C_6$-haloalkyl, $C_3$–$C_6$-alkenyl, $C_1$–$C_6$-alkoxy and ($C_1$–$C_6$-alkoxy)carbonyl;

Y is oxygen, sulfur or —N($R^{27}$)—;

$R^{27}$ is hydrogen, hydroxyl, $C_1$–$C_6$-alkyl, $C_3$–$C_6$-alkenyl, $C_3$-$C_6$-alkynyl, $C_3$–$C_7$-cycloalkyl, $C_1$–$C_6$-haloalkyl, $C_1$–$C_6$-alkoxy-$C_1$–$C_6$-alkyl, $C_1$–$C_6$-alkoxy, $C_3$–$C_6$-alkenyloxy, $C_3$–$C_6$-alkynyloxy, $C_3$–$C_6$cycloalkoxy, $C_5$–$C_7$-cycloalkenyloxy $C_1$–$C_6$-haloalkoxy, $C_3$–$C_6$-haloalkenyloxy, hydroxy-$C_1$–$C_6$-alkoxy, cyano-$C_1$–$C_6$-alkoxy, $C_3$–$C_6$-cycloalkyl-$C_1$–$C_6$-alkoxy, $C_1$–$C_6$-alkoxy-$C_1$–$C_6$-alkoxy, $C_1$–$C_6$-alkoxy -$C_3$–$C_6$-alkenyloxy, ($C_1$–$C_6$-alkyl)carbonyloxy, ($C_1$–$C_6$-haloalkyl)carbonyloxy, ($C_1$–$C_6$-alkyl)carbamoyloxy, ($C_1$–$C_6$-haloalkyl)carbamoyloxy, ($C_1$–$C_6$-alkyl)carbonyl-$C_1$–$C_6$-alkyl, ($C_1$–$C_6$-alkyl)carbonyl-$C_1$–$C_6$-alkoxy, ($C_1$–$C_6$-alkoxy)carbonyl-$C_1$–$C_6$-alkyl, ($C_1$–$C_6$-alkoxy)carbonyl-$C_1$–$C_6$-alkoxy, $C_1$–$C_6$-alkylthio-$C_1$–$C_6$-alkoxy, di($C_1$–$C_6$-alkyl)amino-$C_1$–$C_6$-alkoxy, phenyl, which is unsubstituted or carries one to three substituents selected from the group consisting of cyano, nitro, halogen, $C_1$–$C_6$-alkyl, $C_1$–$C_6$-haloalkyl, $C_2$–$C_6$-alkenyl, $C_1$–$C_6$-alkoxy and ($C_1$–$C_6$-alkoxy)carbonyl, phenyl-$C_1$–$C_6$-alkoxy, phenyl-$C_3$–$C_6$-alkenyloxy or phenyl-$C_3$–$C_6$-alkynyloxy, where one or two methylene groups of the carbon chains can be replaced by —O—, —S— or —N($C_1$–$C_6$-alkyl)-and where each phenyl ring is unsubstituted or carries one to three substituents selected from the group consisting of cyano, nitro, halogen, $C_1$–$C_6$-alkyl, $C_1$–$C_6$-haloalkyl, $C_2$–$C_6$-alkenyl, $C_1$–$C_6$-alkoxy and ($C_1$–$C_6$-alkoxy)carbonyl, or —N($R^{28}$)$R^{29}$, $R^{28}$ and $R^{29}$ are hydrogen, $C_1$–$C_6$-alkyl, $C_3$–$C_6$-alkenyl, $C_3$–$C_6$-alkynyl, $C_3$–$C_6$-cycloalkyl, $C_1$–$C_6$-haloalkyl, $C_1$–$C_6$-alkoxy -$C_1$–$C_6$-alkyl, ($C_1$–$C_6$-alkyl)carbonyl, ($C_1$–$C_6$-alkoxy)carbonyl, ($C_1$–$C_6$-alkoxy)carbonyl-$C_1$–$C_6$-alkyl, ($C_1$–$C_6$-alkoxy)carbonyl-$C_2$–$C_6$-alkenyl, where the alkenyl chain is unsubstituted or carries one to three halogen and/or cyano radicals, or phenyl which is unsubstituted or carries one to three substituents selected from the group consisting of cyano, nitro, halogen, $C_1$–$C_6$-alkyl, $C_1$–$C_6$-haloalkyl, $C_3$–$C_6$-alkenyl, $C_1$–$C_6$-alkoxy and ($C_1$–$C_6$-alkoxy)carbonyl;

or an agriculaturally useful salt of a compound I.

2. A herbicidal composition comprising a herbicidally active amount of a 1-amino-3-benzyluracil of the formula I or of an agriculturally useful salt of I as defined in claim 1 and an inert liquid or solid carrier and optionally a surfactant.

3. A composition for the desciccationor defoliation of plants, comprising an amount of a 1-amino-3-benzyluracil of the formula I or of an agriculturally useful salt of I as defined in claim 1 such that it acts as a desiccantor defoliant and an inert liquid or solid carrier and optionally a surfactant.

4. A method of controlling undesirable vegetation, which comprises allowing a herbicidally active amount of a 1-amino-3-benzyluracil of the formula I or of an agriculturally useful salt of I as defined in claim 1 to act on plants, their environment or on seed.

5. A method for the desiccationor defoliation of plants, which comprises allowing an amount of a 1-amino-3-benzyluracil of the formula I or of an agriculturally useful salt of I as defined in claim 1 to act on plants such that it acts as a desiccantor defoliant.

6. The 1-amino-3-benzyluracil of the formula I as defined in claim 1, wherein

X is oxygen;

Alk is trifluoromethyl;

$R^1$ and $R^2$ are hydrogen;

$R^3$ is halogen;

$R^4$ is cyano, halogen or $C_1$–$C_4$-alkoxy;

$R^5$ is hydrogen, halogen or $C_1$–$C_4$-alkoxy; and $R^6$ is $C_1$–$C_6$-alkoxy, $C_3$–$C_6$-alkenyloxy or $C_3$–$C_6$-alkynyloxy, where each of these radicals is unsubstituted or caries one of the following substituents:
  phenyl which is unsubstituted or carries one to three substituents selected from the group consisting of halogen, nitro, cyano, $C_1$–$C_6$-alkyl, $C_1$–$C_6$-haloalkyl, $C_1$–$C_6$-alkoxy and ($C_1$–$C_6$-alkoxy)carbonyl,
    —CO—$R^9$, —CO—$OR^9$, —CO—$SR^9$, —CO—N($R^9$)$R^{10}$ or —C($R^{21}$)=N—$OR^{20}$; or is —CY—$R^{11}$, —C($R^{11}$)=C($R^{14}$)—CO—$R^{15}$, —CO—$OR^{19}$, —CO—N($R^{19}$)—$OR^{20}$, —C($R^{11}$)=C($R^{14}$)—CO—N($R^{19}$)—$OR^{20}$, —C($R^{11}$)=C($R^{14}$)—C($R^{21}$)=N—$OR^{20}$, —C($R^{21}$)=N—$OR^{20}$, —N($R^{23}$)$R^{24}$ or —CO—N($R^{23}$)$R^{24}$.

7. The 1-amino-3-benzyluracil of the formula I as defined in claim 1, wherein $R^6$ is $C_1$–$C_6$-alkoxy which carries one of the following substituents: —CO—$OR^9$, —CO—N($R^9$)$R^{10}$, —C($R^{21}$)=N—$OR^{20}$ or phenyl which is substituted by halogen or $C_1$–$C_3$-alkoxy.

8. The 1-amino-3-benzyluracil of the formula I as defined in claim 1, wherein $R^6$ is $C_3$–$C_6$-alkenyloxy or $C_3$–$C_6$-alkynyloxy, where each of these radicals is unsubstituted or caries halogen or —CO—$OR^9$.

9. The 1-amino-3-benzyluracil of the formula I as defined in claim 1, wherein $R^6$ is —CY—$R^{11}$, —C($R^{11}$)=C($R^{14}$)—CO—$R^{15}$, —C($R^{11}$)=C($R^{14}$)—CO—N($R^{19}$)—$OR^{20}$, —C($R^{11}$)=C($R^{14}$)—C($R^{21}$)=N—$OR^{20}$ or -N($R^{23}$)$R^{24}$.

10. The 1-amino-3-benzyluracil of the formula I as defined in claim 1, wherein $R^7$ is hydrogen, $C_1$–$C_6$-alkyl, $C_3$–$C_6$-alkenyl, ($C_1$–$C_6$-alkoxy)carbonyl-$C_1$–$C_6$-alkyl or phenyl which is unsusbtituted or carries one to three radicals selected from the group consisting of halogen, nitro, $C_1$–$C_6$-alkyl, $C_1$–$C_6$-alkoxy and ($C_1$–$C_6$-alkoxy)carbonyl;

$R^8$ is hydrogen, $C_1$–$C_3$-alkyl, $C_1$–$C_3$-alkoxy, ($C_1$–$C_3$-alkoxy)carbonyl-$C_1$–$C_3$-alkoxy or $C_3$–$C_4$-alkenyloxy;

$R^9$ is hydrogen, $C_1$–$C_6$-alkyl, $C_3$–$C_6$-alkenyl, ($C_1$–$C_6$-alkoxy)carbonyl-$C_1$–$C_6$-alkyl or phenyl which is unsubstituted or carries one to three radicals selected from the group consisting of halogen, nitro, $C_1$–$C_6$-alkyl, $C_1$–$C_6$-alkoxy and ($C_1$–$C_6$-alkyl)carbonyl;

$R^{10}$ is hydrogen, $C_1$–$C_3$-alkyl, $C_3$–$C_3$-alkoxy, ($C_1$–$C_3$-alkoxy)carbonyl-$C_1$–$C_3$-alkoxy or $C_3$–$C_4$-alkenyloxy;

$R^{11}$ is hydrogen or methyl;

$R^{12}$ and $R^{13}$ are, independently of one another, $C_1$–$C_6$-alkyl, or together are a saturated or unsaturated 2- to 4-membered carbon chain which can carry an oxo substituent and which can further carry one or two radicals selected from the group consisting of $C_1$–$C_6$-alkyl, $C_2$–$C_6$-alkenyl, $C_2$–$C_6$-alkenyloxy and ($C_1$–$C_6$-alkoxy)carbonyl;

$R^{14}$ is hydrogen, halogen or $C_1$–$C_6$-alkyl;

$R^{15}$ is O—$R^{22}$, $C_1$–$C_4$-alkyl, $C_3$–$C_4$-alkenyl, $C_3$–$C_4$-alkynyl, $C_1$–$C_6$-alkyliminooxy or —N($R^{23}$)$R^{24}$;

$R^{16}$ is hydrogen, halogen or $C_1$–$C_6$-alkyl;

$R^{17}$ is hydrogen, halogen or $C_1$–$C_6$-alkyl;

$R^{18}$ is hydrogen, $C_1$–$C_4$-alkyl or ($C_1$–$C_4$-alkoxy)carbonyl;

$R^{19}$ is hydrogen, $C_1$–$C_3$-alkyl or $C_3$–$C_4$-alkenyl, each of which is unsubstituted or carries one of the following radicals: chlorine, ($C_1$–$C_6$-alkyl)carbonyl, ($C_1$–$C_6$-alkoxy)carbonyl or ($C_3$–$C_6$-alkenyloxy)carbonyl, ($C_1$–$C_6$-alkylamino)carbonyl or di($C_1$–$C_6$-alkyl)aminocarbonyl;

$R^{20}$ is $C_1$–$C_6$-alkyl, $C_3$–$C_6$-alkenyl, $C_3$–$C_6$-alkynyl, ($C_1$–$C_6$-alkyl)carbonyl-$C_1$–$C_6$-alkyl, ($C_1$–$C_6$-alkoxy)carbonyl-$C_1$–$C_6$-alkyl or ($C_1$–$C_6$-alkoxy)carbonyl-$C_2$–$C_6$-alkenyl;

$R^{21}$ is hydrogen, $C_3$–$C_6$-alkynyloxy, ($C_2$–$C_6$-alkynyl)carbonyloxy, methyl, $C_1$–$C_6$-alkoxy, $C_3$–$C_6$-alkenyloxy or ($C_1$–$C_6$-alkyl)carbonyloxy, each of which is unsubstituted or carries one of the following radicals: ($C_1$–$C_6$-alkyl)carbonyl, ($C_1$–$C_6$-alkoxy)carbonyl, ($C_1$–$C_6$-alkylamino)carbonyl or di($C_1$–$C_6$-alkyl)aminocarbonyl, phenoxy or benzyloxy, where each of the phenyl rings is unsubstituted or carries one to three radicals selected from the group consisting of halogen, $C_1$–$C_6$-alkyl, $C_1$–$C_6$-haloalkyl and $C_1$–$C_6$-alkoxy;

$R^{22}$ is hydrogen, $C_1$–$C_3$-alkyl or $C_3$–$C_4$-alkenyl, each of which is unsubstituted or carries one of the following radicals: chlorine, ($C_1$–$C_6$-alkyl)carbonyl, ($C_1$–$C_6$-alkoxy)carbonyl or ($C_3$–$C_6$-alkenyloxy)carbonyl, ($C_1$–$C_6$-alkylamino)carbonyl or di($C_1$–$C_6$-alkyl)aminocarbonyl;

$R^{23}$ and $R^{24}$ are, independently of one another, hydrogen, $C_1$–$C_4$-alkyl, $C_3$–$C_4$-alkenyl, $C_3$–$C_6$-cycloalkyl, ($C_1$–$C_6$-alkyl)carbonyl, ($C_1$–$C_6$-alkoxy)carbonyl, ($C_1$–$C_6$-alkoxy)carbonyl-$C_1$–$C_6$-alkyl, $C_1$–$C_6$-alkylsulfonyl, ($C_1$–$C_6$-alkoxy)carbonyl-$C_1$–$C_6$-alkylsulfonyl or phenylsulfonyl where the phenyl ring is unsubstituted or carries one to three radicals selected from the group consisting of nitro, halogen, $C_1$–$C_6$-alkyl, $C_3$–$C_6$-alkenyl, $C_1$–$C_6$-alkoxy and ($C_1$–$C_6$-alkoxy)carbonyl;

Y is —N($R^{27}$)—; and $R^{27}$ is $C_1$–$C_6$-alkyl, $C_3$–$C_6$-alkenyl, $C_3$–$C_6$-alkynyl, $C_1$–$C_6$-alkoxy, $C_3$–$C_6$-alkenyloxy, $C_3$–$C_6$-alkynyloxy, ($C_1$–$C_6$-alkyl)carbonyloxy, ($C_1$–$C_6$-alkyl)carbamoyloxy, ($C_1$–$C_6$-alkyl)carbonyl-$C_1$–$C_6$-alkoxy, ($C_1$–$C_6$-alkoxy)carbonyl-$C_1$–$C_6$-alkyl, ($C_1$–$C_6$-alkoxy)carbonyl-$C_1$–$C_6$-alkoxy or phenyl where the phenyl ring is unsubstituted or carries one to three radicals selected from the group consisting of nitro, halogen, $C_1$–$C_6$-alkyl, $C_1$–$C_6$-alkoxy and ($C_1$–$C_6$-alkoxy)carbonyl.

11. The 1-amino-3-benzyluracil of the formula I as defined in claim 1, wherein $R^6$ is in the β position.

12. The 1-amino-3-benzyluracil of the formula I as defined in claim 1, wherein $R^6$ is $C_1$–$C_4$-alkoxy which carries one of the following groups: —CO—$OR^9$, —CO—N($R^9$)$R^{10}$ or —C($R^{21}$)=N—$OR^{20}$.

13. The 1-amino-3-benzyluracil of the formula I as defined in claim 1, wherein $R^6$ is —CY—$R^{11}$.

14. The 1-amino-3-benzyluracil of the formula I as defined in claim 1, wherein $R^6$ is —C($R^{11}$)=C($R^{14}$)—CO—$R^{15}$, —C($R^{11}$)=C($R^{14}$)—CO—N($R^{19}$)—$OR^{20}$ or —C($R^{11}$)=C($R^{14}$)—C($R^{21}$)=N—$OR^{20}$.

15. An enamine ester of the formula III

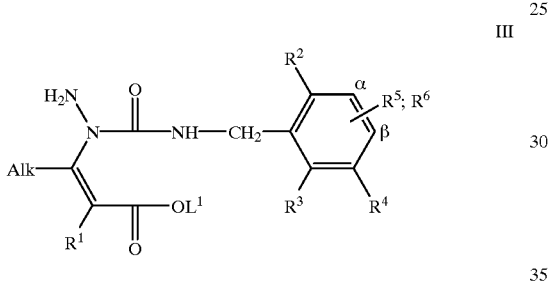

where $L^1$ is $C_1$–$C_6$-alkyl or phenyl and

Alk is $C_1$–$C_4$-haloalkyl;

$R^1$ is hydrogen or halogen;

$R^2$ and $R^3$ independently of one another are hydrogen, cyano, thiocyanato, halogen, $C_1$–$C_4$-haloalkyl, $C_1$–$C_4$-haloalkoxy or $C_1$–$C_4$-haloalkylthio;

$R^4$ is hydrogen, cyano, thiocyanato, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-haloalkylthio or $C_1$–$C_6$-alkylaminocarbonyl;

$R^5$ in the α or β position is hydrogen, cyano, nitro, hydroxyl, amino, halogen, $C_1$–$C_4$-alkylamino which is unsubstituted or substituted by $C_1$–$C_4$-alkyl, ($C_1$–$C_4$-alkyl)carbonyl or ($C_1$–$C_4$-alkoxy)carbonyl, $C_1$–$C_6$-haloalkoxy, $C_1$–$C_6$-haloalkylthio, $C_1$–$C_6$-alkoxy, $C_1$–$C_6$-alkylthio, $C_3$–$C_6$-cycloalkoxy, $C_3$–$C_6$-cycloalkylthio, $C_3$–$C_6$-alkenyloxy, $C_3$–$C_6$-alkenylthio, $C_3$–$C_6$-alkynyloxy, $C_3$–$C_6$-alkynylthio, ($C_1$–$C_6$-alkyl)carbonyloxy, ($C_1$–$C_6$-alkyl)carbonylthio, ($C_3$–$C_6$-alkenyl)carbonyloxy, ($C_3$–$C_6$-alkenyl)carbonylthio, ($C_3$–$C_6$-alkynyl)carbonyloxy, ($C_3$–$C_6$-alkynyl)carbonylthio, $C_1$–$C_6$-alkylsulfonyloxy or $C_1$–$C_6$-alkylsulfonyl, where the last mentioned 16 radicals are unsubstituted or carry one to three substituents selected from the group consisting of
halogen, nitro, cyano, hydroxy, $C_3$–$C_6$-cycloalkyl, $C_1$–$C_6$-alkoxy, $C_3$–$C_6$-cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, $C_1$–$C_6$-alkylsulfinyl, $C_1$–$C_6$-alkylsulfonyl, $C_1$–$C_6$-alkylideneaminoxy, phenyl, phenoxy and phenylsulfonyl which are unsubstituted or carry one to three substituents selected from the group consisting of halogen, nitro, cyano, $C_1$–$C_6$-alkyl, $C_1$–$C_6$-alkoxy and $C_1$–$C_6$-haloalkyl, —CO—$R^7$, —COO$R^7$, —COS$R^7$, —CON($R^7$)$R^8$, —OCO—$R^7$, —OCOO$R^7$, —OCOS$R^7$, —OCON($R^7$)$R^8$ and —N($R^7$)$R^8$, $R^6$ in the α position, in which case $R^5$ is in the β position, or in the β position, in which case $R^5$ is in the α position, is hydrogen, hydroxyl, mercapto, halogen, $C_1$–$C_6$-haloalkoxy, $C_1$–$C_6$-haloalkylthio, $C_1$–$C_6$-alkylthio-($C_1$–$C_6$-alkyl)carbonyl, ($C_1$–$C_6$-alkyl)iminooxycarbonyl, $C_1$–$C_6$-alkoxy, $C_1$–$C_6$-alkylthio, $C_3$–$C_6$-cycloalkoxy, $C_3$–$C_6$-cycloalkylthio, $C_2$–$C_6$-alkenyloxy, $C_2$–$C_6$-alkenylthio, $C_2$–$C_6$-alkynyloxy, $C_2$–$C_6$-alkynylthio, ($C_1$–$C_6$-alkyl)carbonyloxy, ($C_1$–$C_6$-alkyl)carbonylthio, ($C_1$–$C_6$-alkoxy)carbonyloxy, ($C_2$–$C_6$-alkenyl)carbonyloxy, ($C_2$–$C_6$-alkenyl)carbonylthio, ($C_2$–$C_6$-alkynyl)carbonyloxy, ($C_2$–$C_6$-alkynyl)carbonylthio, $C_1$–$C_6$-alkylsulfonyloxy or $C_1$–$C_6$-alkylsulfonyl, where each of the last-mentioned 17 radicals is unsubstituted or carries one to three substituents selected from the group consisting of halogen, nitro, cyano, hydroxy, $C_3$–$C_6$-cycloalkyl, $C_1$–$C_6$-alkoxy, $C_3$–$C_6$-cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, $C_1$–$C_6$-alkylsulfinyl, $C_1$–$C_6$-alkylsulfonyl, $C_1$–$C_6$-alkylideneaminoxy, phenyl, phenoxy and phenylsulfonyl which are unsubstituted or carry one to three substituents selected from the group consisting of halogen, nitro, cyano, $C_1$–$C_6$-alkyl, $C_1$–$C_6$-haloalkyl, $C_1$–$C_6$-alkoxy and ($C_1$–$C_6$-alkoxy)carbonyl, —CO—$R^9$, —COO$R^9$, —COS$R^9$, —CON($R^9$)$R^{10}$, —OCO—$R^9$, —OCOO$R^9$, —OCOS$R^9$, —OCON($R^9$)$R^{10}$ and —N($R^9$)$R^{10}$, and the group —C($R^{21}$)=N—$OR^{20}$; —CY—$R^{11}$, —C($R^{11}$)($Z^1R^{12}$)($Z^2R^{13}$), —C($R^{11}$)=C($R^{14}$)—CN, —C($R^{11}$)=C($R^{14}$)—CO—$R^{15}$, —CH($R^{11}$)—CH($R^{14}$)—CO—$R^{15}$, —C($R^{11}$)=C($R^{14}$)—$CH_2$—CO—$R^{15}$, —C($R^{11}$)=C($R^{14}$)—C($R^{16}$)=C($R^{17}$)—CO—$R^{15}$, —C($R^{11}$)=C($R^{14}$)—$CH_2$—CH($R^{18}$)—CO—$R^{15}$, —CO—$OR^{19}$, —CO—$SR^{19}$, —CO—N($R^{19}$)—$OR^{20}$, —C≡C—CO—N($R^{19}$)—$OR^{20}$, —C≡C—CS—N($R^{19}$)—$OR^{20}$, —C($R^{11}$)=C($R^{14}$)—CO—N($R^{19}$)—$OR^{20}$, —C($R^{11}$)=C($R^{14}$)—CS—N($R^{19}$)—$OR^{20}$, —C($R^{11}$)=C($R^{14}$)—C($R^{21}$)=N—$OR^{20}$, —C($R^{21}$)=N—$OR^{20}$, —C≡C—C($R^{21}$)=N—$OR^{20}$, —C($Z^1R^{12}$)($Z^2R^{13}$)—$OR^{19}$, —C($Z^1R^{12}$)($Z^2R^{13}$)—$SR^{19}$, —C($Z^1R^{12}$)($Z^2R^{13}$)—N($R^{23}$)$R^{24}$; —N($R^{23}$)$R^{24}$, —CON($R^{23}$)$R^{24}$,

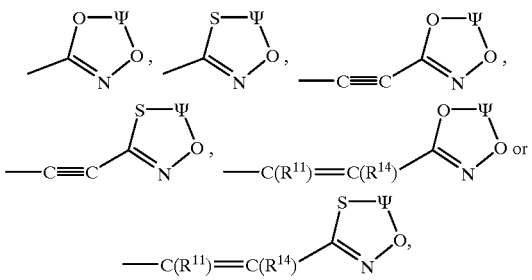

$Z^1$ and $Z^2$ are oxygen or sulfur,

Ψ is $C_1$–$C_3$-alkylene which is unsubstituted or carries a $C_1$–$C_6$-alkyl substituent;

$R^7$ and $R^9$ are hydrogen, $C_1$–$C_6$-alkyl, $C_3$–$C_6$-cycloalkyl, $C_3$–$C_6$-alkenyl, $C_3$–$C_6$-alkynyl, $C_1$–$C_6$-alkoxy-$C_1$–$C_6$-alkyl, ($C_1$–$C_6$-alkoxy)carbonyl-$C_1$–$C_6$-alkyl, ($C_3$–$C_6$-alkenyloxy)carbonyl-$C_1$–$C_6$-alkyl, phenyl or phenyl-$C_1$–$C_6$-alkyl, where the phenyl group and the phenyl ring of the phenyl alkyl group is unsubstituted or carries one to three radicals selected from the group consisting of halogen, nitro, cyano, $C_1$–$C_6$-alkyl, $C_1$–$C_6$-haloalkyl, $C_1$–$C_6$-alkoxy and ($C_1$–$C_6$-alkyl)carbonyl, $R^8$ and $R^{10}$ are hydrogen, hydroxyl, $C_1$–$C_6$-alkyl, $C_3$–$C_6$-cycloalkyl, $C_1$–$C_6$-alkoxy, ($C_1$–$C_6$-alkoxy)carbonyl-$C_1$–$C_6$-alkoxy, $C_3$–$C_6$-alkenyl or $C_3$–$C_6$-alkenyloxy $R^{11}$ is hydrogen, cyano, $C_1$–$C_6$-alkyl, $C_1$–$C_6$-haloalkyl, $C_2$–$C_6$-alkenyl, $C_2$–$C_6$-alkynyl, $C_3$–$C_6$-cycloalkyl, $C_1$–$C_6$-alkoxy-$C_1$–$C_6$-alkyl or ($C_1$–$C_6$-alkoxy)carbonyl;

$R^{12}$ and $R^{13}$ independently of one another are $C_1$–$C_6$-alkyl, $C_1$–$C_6$-haloalkyl, $C_3$–$C_6$-alkenyl, $C_3$–$C_6$-alkynyl, $C_1$–$C_6$-alkoxy-$C_1$–$C_6$-alkyl, or $R^{12}$ and $R^{13}$ together are a saturated or unsaturated, 2- to 4-membered carbon chain which is unsubstituted or carries one to three radicals selected from the group consisting of cyano, nitro, amino, halogen, $C_1$–$C_6$-alkyl, $C_2$–$C_6$-alkenyl, $C_1$–$C_6$-alkoxy, $C_2$–$C_6$-alkenyloxy, $C_2$–$C_6$-alkynyloxy, $C_1$–$C_6$-haloalkyl, cyano-$C_1$–$C_6$-alkyl, hydroxy-$C_1$–$C_6$-alkyl, $C_1$–$C_6$-alkoxy-$C_1$–$C_6$-alkyl, $C_3$–$C_6$-alkenyloxy-$C_1$–$C_6$-alkyl, $C_3$–$C_6$-alkynyloxy-$C_1$–$C_6$-alkyl, $C_3$–$C_6$-cycloalkyl, $C_3$–$C_6$-cycloalkoxy, carboxyl, ($C_1$–$C_6$-alkoxy)carbonyl, ($C_1$–$C_6$-alkyl)carbonyloxy-$C_1$–$C_6$-alkyl and phenyl which is unsubstituted or carries one to three substituents selected from the group consisting of cyano, nitro, amino, halogen, $C_1$–$C_6$-alkyl, $C_1$–$C_6$-haloalkyl, $C_1$–$C_6$-alkoxy and ($C_1$–$C_6$-alkoxy)carbonyl, and where the carbon chain can also carry an oxo group, a fused or spiro-linked 3- to 7-membered carbon ring which is unsubstituted or carries one or two of the following substituents: cyano, $C_1$–$C_6$-alkyl, $C_2$–$C_6$-alkenyl, $C_1$–$C_6$-alkoxy, cyano-$C_1$–$C_6$-alkyl, $C_1$–$C_6$-haloalkyl and ($C_1$–$C_6$-alkoxy)carbonyl;

$R^{14}$ is hydrogen, cyano, halogen, $C_1$–$C_6$-alkyl, $C_1$–$C_6$-haloalkyl, $C_1$–$C_6$-alkoxy, ($C_1$–$C_6$-alkyl)carbonyl or ($C_1$–$C_6$-alkoxy)carbonyl;

$R^{15}$ is hydrogen, O—$R^{22}$, S—$R^{22}$, $C_1$–$C_6$-alkyl which is unsubstituted or carries one or two $C_1$–$C_6$-alkoxy substituents, or is $C_2$–$C_6$-alkenyl, $C_2$–$C_6$-alkynyl, $C_1$–$C_6$-haloalkyl, $C_3$–$C_6$-cycloalkyl, $C_1$–$C_6$-alkylthio-$C_1$–$C_6$-alkyl, $C_1$–$C_6$-alkyliminooxy, —N($R^{23}$)$R^{24}$ or phenyl which is unsubstituted or carries one to three substituents selected from the group consisting of cyano, nitro, halogen, $C_1$–$C_6$-alkyl, $C_2$–$C_6$-alkenyl, $C_1$–$C_6$-haloalkyl, $C_1$–$C_6$-alkoxy and ($C_1$–$C_6$-alkoxy)carbonyl, $R^{16}$ is hydrogen, cyano, halogen, $C_1$–$C_6$-alkyl, $C_3$–$C_6$-alkenyl, $C_3$–$C_6$-alkynyl, $C_1$–$C_6$-alkoxy-$C_1$–$C_6$-alkyl, ($C_1$–$C_6$-alkyl)carbonyl, ($C_1$–$C_6$-alkoxy)carbonyl, —N($R^{25}$)$R^{26}$, or is phenyl which is unsubstituted or carries one to three substituents selected from the group consisting of cyano, nitro, halogen, $C_1$–$C_6$-alkyl, $C_1$–$C_6$-haloalkyl, $C_3$–$C_6$-alkenyl, $C_1$–$C_6$-alkoxy and ($C_1$–$C_6$-alkoxy)carbonyl;

$R^{17}$ is hydrogen, cyano, halogen, $C_1$–$C_6$-alkyl, $C_1$–$C_6$-alkoxy, $C_1$–$C_6$-haloalkyl, ($C_1$–$C_6$-alkyl)carbonyl or ($C_1$–$C_6$-alkoxy)carbonyl;

$R^{18}$ is hydrogen, cyano, $C_1$–$C_6$-alkyl or ($C_1$–$C_6$-alkoxy)carbonyl;

$R^{19}$ is hydrogen, $C_1$–$C_6$-alkyl, $C_1$–$C_6$-haloalkyl, $C_2$–$C_6$-alkenyl or $C_2$–$C_6$-alkynyl, where each of the last mentioned 4 groups is unsubstituted or carries one or two of the following radicals: cyano, halogen, hydroxyl, hydroxycarbonyl, $C_1$–$C_6$-alkoxy, $C_1$–$C_6$-alkylthio, ($C_1$–$C_6$-alkyl)carbonyl, ($C_1$–$C_6$-alkoxy)carbonyl, ($C_1$–$C_6$-alkyl)carbonyloxy, ($C_3$–$C_6$-alkenyloxy)carbonyl; or is ($C_1$–$C_6$-alkyl)carbonyl, ($C_1$–$C_6$-haloalkyl)carbonyl, ($C_1$–$C_6$-alkoxy)carbonyl, $C_1$–$C_6$-alkylaminocarbonyl, di($C_1$–$C_6$-alkyl)aminocarbonyl, $C_1$–$C_6$-alkyloximino-$C_1$–$C_6$-alkyl, $C_3$–$C_6$-cycloalkyl, phenyl or phenyl-$C_1$–$C_6$-alkyl, where the phenyl rings are unsubstituted or carry one to three substituents selected from the group consisting of cyano, nitro, halogen, $C_1$–$C_6$-alkyl, $C_1$–$C_6$-haloalkyl, $C_1$–$C_6$-alkoxy and ($C_1$–$C_6$-alkoxy)carbonyl;

$R^{20}$ is hydrogen, $C_1$–$C_6$-alkyl, $C_1$–$C_6$-haloalkyl, $C_3$–$C_6$-cycloalkyl, $C_3$–$C_6$-alkenyl, $C_3$–$C_6$-alkynyl, hydroxy-$C_1$–$C_6$-alkyl, $C_1$–$C_6$-alkoxy-$C_1$–$C_6$-alkyl, $C_1$–$C_6$-alkylthio-$C_1$–$C_6$-alkyl, cyano-$C_1$–$C_6$-alkyl, ($C_1$–$C_6$-alkyl)carbonyl-$C_1$–$C_6$-alkyl, ($C_1$–$C_6$-alkoxy)-carbonyl-$C_1$–$C_6$-alkyl, ($C_1$–$C_6$-alkoxy)carbonyl-$C_2$–$C_6$-alkenyl, ($C_1$–$C_6$-alkyl)carbonyloxy-$C_1$–$C_6$-alkyl or phenyl-$C_1$–$C_6$-alkyl, where the phenyl ring is unsubstituted or carries one to three substituents selected from the group consisting of cyano, nitro, halogen, $C_1$–$C_6$-alkyl, $C_1$–$C_6$-haloalkyl, $C_1$–$C_6$-alkoxy and ($C_1$–$C_6$-alkoxy)carbonyl;

$R^{21}$ is hydrogen, halogen, $C_1$–$C_6$-alkyl, $C_1$–$C_6$-haloalkyl, $C_1$–$C_6$-alkoxy, $C_1$–$C_6$-haloalkoxy, $C_3$–$C_6$-alkenyloxy, $C_1$–$C_6$-alkylthio, $C_1$–$C_6$-haloalkylthio, ($C_1$–$C_6$-alkyl)carbonyloxy, ($C_1$–$C_6$-haloalkyl)carbonyloxy, $C_1$–$C_6$-alkylsulfonyloxy or $C_1$–$C_6$-haloalkylsulfonyloxy, where the last mentioned 11 radicals are unsubstituted or carry one of the following substituents: hydroxyl, cyano, hydroxycarbonyl, $C_1$–$C_6$-alkoxy, $C_1$–$C_6$-alkylthio, ($C_1$–$C_6$-alkyl)carbonyl, ($C_1$–$C_6$-alkoxy) carbonyl, ($C_1$–$C_6$-alkyl)aminocarbonyl, di($C_1$–$C_6$-alkyl)aminocarbonyl or ($C_1$–$C_6$-alkyl)carbonyloxy, ($C_1$–$C_6$-alkyl)carbonyl, ($C_1$–$C_6$-haloalkyl)carbonyl, ($C_1$–$C_6$-alkoxy)carbonyl, ($C_1$–$C_6$-alkoxy)carbonyloxy, ($C_1$–$C_6$-alkyl)carbonylthio, ($C_1$–$C_6$haloalkyl) carbonylthio, ($C_1$–$C_6$-alkoxy)carbonylthio, $C_2$–$C_6$-alkenyl, $C_2$–$C_6$-alkenylthio, $C_3$–$C_6$-alkynyl, $C_3$–$C_6$-alkynyloxy, $C_3$–$C_6$-alkynylthio, ($C_2$–$C_6$-alkynyl)carbonyloxy, $C_3$–$C_6$-alkynylsulfonyloxy, $C_3$–$C_6$-cycloalkyl, $C_3$–$C_6$-cycloalkoxy, $C_3$–$C_6$-cycloalkylthio, ($C_3$–$C_6$-cycloalkyl)carbonyloxy, $C_3$–$C_6$-cycloalkylsulfonyloxy, phenyl, phenoxy, phenylthio, benzoyloxy, phenylsulfonyloxy, phenyl-$C_1$–$C_6$-alkyl, phenyl-$C_1$–$C_6$-alkoxy, phenyl-$C_1$–$C_6$-alkylthio, phenyl-($C_1$–$C_6$-alkyl)carbonyloxy or phenyl-($C_1$–$C_6$-alkyl)sulfonyloxy, where the phenyl rings of the last-mentioned 10 radicals are unsubstituted or carry one to three substituents selected from the group consisting of cyano, nitro, halogen, $C_1$–$C_6$-alkyl, $C_1$–$C_6$-haloalkyl, $C_1$–$C_6$-alkoxy and ($C_1$–$C_6$-alkoxy)carbonyl;

$R^{22}$ having one of the meanings of $R^{19}$;

$R^{23}$, $R^{24}$, $R^{25}$ and $R^{26}$ independently of one another are hydrogen, $C_1$–$C_6$-alkyl, $C_2$–$C_6$-alkenyl, $C_2$–$C_6$-alkynyl, $C_3$–$C_6$-cycloalkyl, $C_1$–$C_6$-haloalkyl, $C_1$–$C_6$-alkoxy-$C_1$–$C_6$-alkyl, ($C_1$–$C_6$-alkyl)carbonyl, ($C_1$–$C_6$-alkoxy)carbonyl, ($C_1$–$C_6$-alkoxy)carbonyl-$C_1$–$C_6$-alkyl, ($C_1$–$C_6$-alkoxy)carbonyl-$C_2$–$C_6$-alkenyl, where the alkenyl chain is unsubstituted or carries one to three halogen and/or cyano radicals, or are $C_1$–$C_6$-alkylsulfonyl, ($C_1$–$C_6$-alkoxy)carbonyl-$C_1$–$C_6$- alkylsulfonyl, phenyl or phenylsulfonyl, where the two phenyl rings are unsubstituted or carry one to three substituents selected from the group consisting of cyano, nitro, halogen, $C_1$–$C_6$-alkyl, $C_1$–$C_6$-haloalkyl, $C_3$–$C_6$-alkenyl, $C_1$–$C_6$-alkoxy and ($C_1$–$C_6$-alkoxy) carbonyl Y is oxygen, sulfur or —N($R^{27}$)—;

$R^{27}$ is hydrogen, hydroxyl, $C_1$–$C_6$-alkyl, $C_3$–$C_6$-alkenyl, $C_3$–$C_6$-alkynyl, $C_3$–$C_7$-cycloalkyl, $C_1$–$C_6$-haloalkyl, $C_1$–$C_6$-alkoxy-$C_1$–$C_6$-alkyl, $C_1$–$C_6$-alkoxy, $C_3$–$C_6$-alkenyloxy, $C_3$–$C_6$-alkynyloxy, $C_3$–$C_6$-cycloalkoxy, $C_5$–$C_7$-cycloalkenyloxy, $C_1$–$C_6$-haloalkoxy, $C_3$–$C_6$-haloalkenyloxy, hydroxy-$C_1$–$C_6$-alkoxy, cyano-$C_1$–$C_6$-alkoxy, $C_3$–$C_6$-cycloalkyl-$C_1$–$C_6$-alkoxy, $C_1$–$C_6$-alkoxy-$C_1$–$C_6$-alkoxy, $C_1$–$C_6$-alkoxy-$C_3$–$C_6$-alkenyloxy, ($C_1$–$C_6$-alkyl)carbonyloxy, ($C_1$–$C_6$-haloalkyl)carbonyloxy, ($C_1$–$C_6$-alkyl)carbamoyloxy, ($C_1$–$C_6$-haloalkyl)carbamoyloxy, ($C_1$–$C_6$-alkyl)carbonyl-$C_1$–$C_6$-alkyl, ($C_1$–$C_6$-alkyl)carbonyl-$C_1$–$C_6$-alkoxy, ($C_1$–$C_6$-alkoxy)carbonyl-$C_1$–$C_6$-alkyl, ($C_1$–$C_6$-alkoxy)carbonyl-$C_1$–$C_6$-alkoxy, $C_1$–$C_6$-alkylthio-$C_1$–$C_6$-alkoxy, di($C_1$–$C_6$-alkyl)amino-$C_1$–$C_6$-alkoxy, phenyl, which is unsubstituted or carries one to three substituents selected from the group consisting of cyano, nitro, halogen, $C_1$–$C_6$-alkyl, $C_1$–$C_6$-haloalkyl, $C_2$–$C_6$-alkenyl, $C_1$–$C_6$-alkoxy and ($C_1$–$C_6$-alkoxy) carbonyl, phenyl-$C_1$–$C_6$-alkoxy, phenyl-$C_3$–$C_6$-alkenyloxy or phenyl-$C_3$–$C_6$-alkynyloxy, where one or two methylene groups of the carbon chains can be replaced by —O—, —S— or —N($C_1$–$C_6$-alkyl)— and where each phenyl ring is unsubstituted or carries one to three substituents selected from the group consisting of cyano, nitro, halogen, $C_1$–$C_6$-alkyl, $C_1$–$C_6$-haloalkyl, $C_2$–$C_6$-alkenyl, $C_1$–$C_6$-alkoxy and ($C_1$–$C_6$-alkoxy)carbonyl, or —N($R^{28}$)$R^{29}$, $R^{28}$ and $R^{29}$ are hydrogen, $C_1$–$C_6$-alkyl, $C_3$–$C_6$-alkenyl, $C_3$–$C_6$-alkynyl, $C_3$–$C_6$-cycloalkyl, $C_1$–$C_6$-haloalkyl, $C_1$–$C_6$-alkoxy-$C_1$–$C_6$-alkyl, ($C_1$–$C_6$-alkyl)carbonyl, ($C_1$–$C_6$-alkoxy)carbonyl, ($C_1$–$C_6$-alkoxy)carbonyl-$C_1$–$C_6$-alkyl, ($C_1$–$C_6$-alkoxy)carbonyl-$C_2$–$C_6$-alkenyl, where the alkenyl chain is unsubstituted or carries one to three halogen and/or cyano radicals, or phenyl which is unsubstituted or carries one to three substituents selected from the group consisting of cyano, nitro, halogen, $C_1$–$C_6$-alkyl, $C_1$–$C_6$-haloalkyl, $C_3$–$C_6$-alkenyl, $C_1$–$C_6$-alkoxy and ($C_1$–$C_6$-alkoxy)carbonyl.

16. An enamine carboxylate of the formula IV

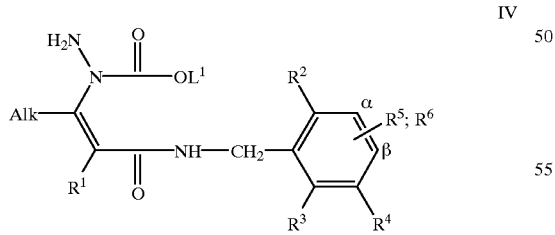

where $L^1$ is $C_1$–$C_6$-alkyl or phenyl and
Alk is $C_1$–$C_4$-haloalkyl;
$R^1$ is hydrogen or halogen;
$R^2$ and $R^3$ independently of one another are hydrogen, cyano, thiocyanato, halogen, $C_1$–$C_4$-haloalkyl, $C_1$–$C_4$-haloalkoxy or $C_1$–$C_4$-haloalkylthio;
$R^4$ is hydrogen, cyano, thiocyanato, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-haloalkylthio or $C_1$–$C_6$-alkylaminocarbonyl;

$R^5$ in the α or β position is hydrogen, cyano, nitro, hydroxyl, amino, halogen, $C_1$–$C_4$-alkylamino which is unsubstituted or substituted by $C_1$–$C_4$-alkyl, ($C_1$–$C_4$-alkyl)carbonyl or ($C_1$–$C_4$-alkoxy)carbonyl, $C_1$–$C_6$-haloalkoxy, $C_1$–$C_6$-haloalkylthio, $C_1$–$C_6$-alkoxy, $C_1$–$C_6$-alkylthio, $C_3$–$C_6$-cycloalkoxy, $C_3$–$C_6$-cycloalkylthio, $C_3$–$C_6$-alkenyloxy, $C_3$–$C_6$-alkenylthio, $C_3$–$C_6$-alkynyloxy, $C_3$–$C_6$-alkynylthio, ($C_1$–$C_6$-alkyl)carbonyloxy, ($C_1$–$C_6$-alkyl)carbonylthio, ($C_3$–$C_6$-alkenyl)carbonyloxy, ($C_3$–$C_6$-alkenyl)carbonylthio, ($C_3$–$C_6$-alkynyl)carbonyloxy, ($C_3$–$C_6$-alkynyl)carbonylthio, $C_1$–$C_6$-alkylsulfonyloxy or $C_1$–$C_6$-alkylsulfonyl, where the last mentioned 16 radicals are unsubstituted or carry one to three substituents selected from the group consisting of
halogen, nitro, cyano, hydroxy, $C_3$–$C_6$-cycloalkyl, $C_1$–$C_6$-alkoxy, $C_3$–$C_6$-cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, $C_1$–$C_6$-alkylsulfinyl, $C_1$–$C_6$-alkylsulfonyl, $C_1$–$C_6$-alkylideneaminoxy,
phenyl, phenoxy and phenylsulfonyl which are unsubstituted or carry one to three substituents selected from the group consisting of halogen, nitro, cyano, $C_1$–$C_6$-alkyl, $C_1$–$C_6$-alkoxy and $C_1$–$C_6$-haloalkyl,
—CO—$R^7$, —COO$R^7$, —COS$R^7$, —CON($R^7$)$R^8$, —OCO—$R^7$, —OCOO$R^7$, —OCOS$R^7$, —OCON($R^7$)$R^8$ and —N($R^7$)$R^8$, $R^6$ in the α position, in which case $R^5$ is in the β position, or in the β position, in which case $R^5$ is in the α position, is hydrogen, hydroxyl, mercapto, halogen, $C_1$–$C_6$-haloalkoxy, $C_1$–$C_6$-haloalkylthio, $C_1$–$C_6$-alkylthio-($C_1$–$C_6$-alkyl)carbonyl, ($C_1$–$C_6$-alkyl)iminooxycarbonyl, $C_1$–$C_6$-alkoxy, $C_1$–$C_6$-alkylthio, $C_3$–$C_6$-cycloalkoxy, $C_3$–$C_6$-cycloalkylthio, $C_2$–$C_6$-alkenyloxy, $C_2$–$C_6$-alkenylthio, $C_2$–$C_6$-alkynyloxy, $C_2$–$C_6$-alkynylthio, ($C_1$–$C_6$-alkyl)carbonyloxy, ($C_1$–$C_6$-alkyl)carbonylthio, ($C_1$–$C_6$-alkoxy) carbonyloxy, ($C_2$–$C_6$-alkenyl)carbonyloxy, ($C_2$–$C_6$-alkenyl)carbonylthio, ($C_2$–$C_6$-alkynyl)carbonyloxy, ($C_2$–$C_6$-alkynyl)carbonylthio, $C_1$–$C_6$-alkylsultonyloxy or $C_1$–$C_6$-alkylsulfonyl, where each of the last-mentioned 17 radicals is unsubstituted or carries one to three substituents selected from the group consisting of
halogen, nitro, cyano, hydroxy, $C_3$–$C_6$-cycloalkyl, $C_1$–$C_6$-alkoxy, $C_3$–$C_6$-cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, $C_1$–$C_6$-alkylsulfinyl, $C_1$–$C_6$-alkylsulfonyl, $C_1$–$C_6$-alkylideneaminoxy,
phenyl, phenoxy and phenylsulfonyl which are unsubstituted or carry one to three substituents selected from the group consisting of halogen, nitro, cyano, $C_1$–$C_6$-alkyl, $C_1$–$C_6$-haloalkyl, $C_1$–$C_6$-alkoxy and ($C_1$–$C_6$-alkoxy)carbonyl,
—CO—$R^9$, —COO$R^9$, —COS$R^9$, —CON($R^9$)$R^{10}$, —OCO—$R^9$, —OCOO$R^9$, —OCOS$R^9$, —OCON($R^9$)$R^{10}$ and —N($R^9$)$R^{10}$, and
the group —C($R^{21}$)=N—O$R^{20}$; —CY—$R^{11}$, —C($R^{11}$)($Z^1R^{12}$)($Z^2R^{13}$), —C($R^{11}$)=C($R^{14}$)—CN, —C($R^{11}$)=C($R^{14}$), —CO—$R^{15}$, —CH($R^{11}$)—CH($R^{14}$)—CO—$R^{15}$, —C($R^{11}$)=C($R^{14}$)—CH$_2$—CO—$R^{15}$, —C($R^{11}$)=C($R^{14}$)—C($R^{16}$)=C($R^{17}$)—CO—$R^{15}$, —C($R^{11}$)=C($R^{14}$)—CH$_2$—CH($R^{18}$)—CO—$R^{15}$, —CO—O$R^{19}$, —CO—S$R^{19}$, —CO—N $(R^{19})$—$OR^{20}$, —C≡C—CO—$N(R^{19})$—$OR^{20}$, —C≡C—CS—$N(R^{19})$—$OR^{20}$, —$C(R^{11})$=C$(R^{14})$—CO—$N(R^{19})$—$OR^{20}$, —$C(R^{11})$=$C(R^{14})$—CS—$N(R^{19})$—$OR^{20}$, —$C(R^{11})$=$C(R^{14})$—$C(R^{21})$=N—$OR^{20}$, —$C(R^{21})$=N—$OR^{20}$, —C≡C—C$(R^{21})$=N—$OR^{20}$, —$C(Z^1R^{12})(Z^2R^{13})$—$OR^{19}$, —$C(Z^1R^{12})$-$(Z^2R^{13})$—$SR^{19}$, —$C(Z^1R^{12})(Z^2R^{13})$—$N(R^{23})R^{24}$, —$N(R^{23})R^{24}$, —$CON(R^{23})R^{24}$,

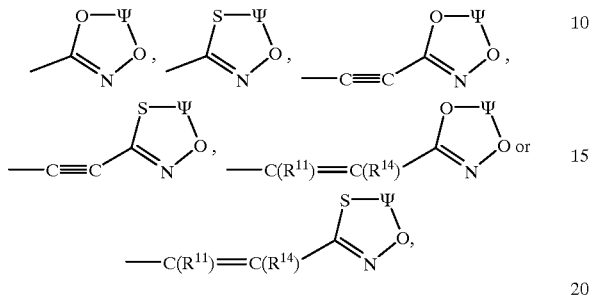

$Z^1$ and $Z^2$ are oxygen or sulfur,

Ψ is $C_1$–$C_3$-alkylene which is unsubstituted or carries a $C_1$–$C_6$-alkyl substituent;

$R^7$ and $R^9$ are hydrogen, $C_1$–$C_6$-alkyl, $C_3$–$C_6$-cycloalkyl, $C_3$–$C_6$-alkenyl, $C_3$–$C_6$-alknyl, $C_1$–$C_6$-alkoxy-$C_1$–$C_6$-alkyl, $(C_1$–$C_6$-alkoxy)carbonyl-$C_1$–$C_6$-alkyl, $(C_3$–$C_6$-alkenyloxy)carbonyl-$C_1$–$C_6$-alkyl, phenyl or phenyl-$C_1$–$C_6$-alkyl, where the phenyl group and the phenyl ring of the phenyl alkyl group is unsubstituted or carries one to three radicals selected from the group consisting of halogen, nitro, cyano, $C_1$–$C_6$-alkyl, $C_1$–$C_6$-haloalkyl, $C_1$–$C_6$-alkoxy and $(C_1$–$C_6$-alkyl)carbonyl, $R^8$ and $R^{10}$ are hydrogen, hydroxyl, $C_1$–$C_6$-alkyl, $C_3$–$C_6$-cycloalkyl, $C_1$–$C_6$-alkoxy, $(C_1$–$C_6$-alkoxy)carbonyl-$C_1$–$C_6$-alkoxy, $C_3$–$C_6$-alkenyl or $C_3$–$C_6$-alkenyloxy $R^{11}$ is hydrogen, cyano, $C_1$–$C_6$-alkyl, $C_1$–$C_6$-haloalkyl, $C_2$–$C_6$-alkenyl, $C_2$–$C_6$-alkynyl, $C_3$–$C_6$-cycloalkyl, $C_1$–$C_6$-alkoxy-$C_1$–$C_6$-alkyl or $(C_1$–$C_6$-alkoxy)carbonyl;

$R^{12}$ and $R^{13}$ independently of one another are $C_1$–$C_6$-alkyl, $C_1$–$C_6$-haloalkyl, $C_3$–$C_6$-alkenyl, $C_3$–$C_6$-alkynyl, $C_1$–$C_6$-alkoxy-$C_1$–$C_6$-alkyl, or $R^{12}$ and $R^{13}$ together are a saturated or unsaturated, 2- to 4-membered carbon chain which is unsubstituted or carries one to three radicals selected from the group consisting of cyano, nitro, amino, halogen, $C_1$–$C_6$-alkyl, $C_2$–$C_6$-alkenyl, $C_1$–$C_6$-alkoxy, $C_2$–$C_6$-alkenyloxy, $C_2$–$C_6$-alkynyloxy, $C_1$–$C_6$-haloalkyl, cyano-$C_1$–$C_6$-alkyl, hydroxy-$C_1$–$C_6$-alkyl, $C_1$–$C_6$-alkoxy-$C_1$–$C_6$-alkyl, $C_3$–$C_6$-alkenyloxy-$C_1$–$C_6$-alkyl, $C_3$–$C_6$-alkynyloxy-$C_1$–$C_6$-alkyl, $C_3$–$C_6$-cycloalkyl, $C_3$–$C_6$-cycloalkoxy, carboxyl, $(C_1$–$C_6$-alkoxy)carbonyl, $(C_1$–$C_6$-alkyl)carbonyloxy-$C_1$–$C_6$-alkyl and phenyl which is unsubstituted or carries one to three substituents selected from the group consisting of cyano, nitro, amino, halogen, $C_1$–$C_6$-alkyl, $C_1$–$C_6$-haloalkyl, $C_1$–$C_6$-alkoxy and $(C_1$–$C_6$-alkoxy)carbonyl, and where the carbon chain can also carry an oxo group, a fused or spiro-linked 3- to 7-membered carbon ring which is unsubstituted or carries one or two of the following substituents: cyano, $C_1$–$C_6$-alkyl, $C_2$–$C_6$-alkenyl, $C_1$–$C_6$-alkoxy, cyano-$C_1$–$C_6$-alkyl, $C_1$–$C_6$-haloalkyl and $(C_1$–$C_6$-alkoxy)carbonyl;

$R^{14}$ is hydrogen, cyano, halogen, $C_1$–$C_6$-alkyl, $C_1$–$C_6$-haloalkyl, $C_1$–$C_6$-alkoxy, $(C_1$–$C_6$-alkyl)carbonyl or $(C_1$–$C_6$-alkoxy)carbonyl;

$R^{15}$ is hydrogen, O—$R^{22}$, S—$R^{22}$, $C_1$–$C_6$-alkyl which is unsubstituted or carries one or two $C_1$–$C_6$-alkoxy substituents, or is $C_2$–$C_6$-alkenyl, $C_2$–$C_6$-alkynyl, $C_1$–$C_6$-haloalkyl, $C_3$–$C_6$-cycloalkyl, $C_1$–$C_6$-alkylthio-$C_1$–$C_6$-alkyl, $C_1$–$C_6$-alkyliminooxy, —$N(R^{23})R^{24}$ or phenyl which is unsubstituted or carries one to three substituents selected from the group consisting of cyano, nitro, halogen, $C_1$–$C_6$-alkyl, $C_2$–$C_6$-alkenyl, $C_1$–$C_6$-haloalkyl, $C_1$–$C_6$-alkoxy and $(C_1$–$C_6$-alkoxy)carbonyl, $R^{16}$ is hydrogen, cyano, halogen, $C_1$–$C_6$-alkyl, $C_3$–$C_6$-alkenyl, $C_3$–$C_6$-alkynyl, $C_1$–$C_6$-alkoxy-$C_1$–$C_6$-alkyl, $(C_1$–$C_6$-alkyl)carbonyl, $(C_1$–$C_6$-alkoxy)carbonyl, —$N(R^{25})R^{26}$, or is phenyl which is unsubstituted or carries one to three substituents selected from the group consisting of cyano, nitro, halogen, $C_1$–$C_6$-alkyl, $C_1$–$C_6$-haloalkyl, $C_3$–$C_6$-alkenyl, $C_1$–$C_6$-alkoxy and $(C_1$–$C_6$-alkoxy)carbonyl;

$R^{17}$ is hydrogen, cyano, halogen, $C_1$–$C_6$-alkyl, $C_1$–$C_6$-alkoxy, $C_1$–$C_6$-haloalkyl, $(C_1$–$C_6$-alkyl)carbonyl or $(C_1$–$C_6$-alkoxy)carbonyl;

$R^{18}$ is hydrogen, cyano, $C_1$–$C_6$-alkyl or $(C_1$–$C_6$-alkoxy)carbonyl;

$R^{19}$ is hydrogen, $C_1$–$C_6$-alkyl, $C_1$–$C_6$-haloalkyl, $C_2$–$C_6$-alkenyl or $C_2$–$C_6$-alkynyl, where each of the last mentioned 4 groups is unsubstituted or carries one or two of the following radicals: cyano, halogen, hydroxyl, hydroxycarbonyl, $C_1$–$C_6$-alkoxy, $C_1$–$C_6$-alkylthio, $(C_1$–$C_6$-alkyl)carbonyl, $(C_1$–$C_6$-alkoxy)carbonyl, $(C_1$–$C_6$-alkyl)carbonyloxy, $(C_3$–$C_6$-alkenyloxy)carbonyl; or is $(C_1$–$C_6$-alkyl)carbonyl, $(C_1$–$C_6$-haloalkyl)carbonyl, $(C_1$–$C_6$-alkoxy)carbonyl, $C_1$–$C_6$-alkylaminocarbonyl, di$(C_1$–$C_6$-alkyl)aminocarbonyl, $C_1$–$C_6$-alkyloximino-$C_1$–$C_6$-alkyl, $C_3$–$C_6$-cycloalkyl, phenyl or phenyl-$C_1$–$C_6$-alkyl, where the phenyl rings are unsubstituted or carry one to three substituents selected from the group consisting of cyano, nitro, halogen, $C_1$–$C_6$-alkyl, $C_1$–$C_6$-haloalkyl, $C_1$–$C_6$-alkoxy and $(C_1$–$C_6$-alkoxy)carbonyl;

$R^{20}$ is hydrogen, $C_1$–$C_6$-alkyl, $C_1$–$C_6$-haloalkyl, $C_3$–$C_6$-cycloalkyl, $C_3$–$C_6$-alkenyl, $C_3$–$C_6$-alkynyl, hydroxy-$C_1$–$C_6$-alkyl, $C_1$–$C_6$-alkoxy-$C_1$–$C_6$-alkyl, $C_1$–$C_6$-alkylthio-$C_1$–$C_6$-alkyl, cyano-$C_1$–$C_6$-alkyl, $(C_1$–$C_6$-alkyl)carbonyl-$C_1$–$C_6$-alkyl, $(C_1$–$C_6$-alkoxy)carbonyl-$C_1$–$C_6$-alkyl, $(C_1$–$C_6$-alkoxy)carbonyl-$C_2$–$C_6$-alkenyl, $(C_1$–$C_6$-alkyl)carbonyloxy-$C_1$–$C_6$-alkyl or phenyl-$C_1$–$C_6$-alkyl, where the phenyl ring is unsubstituted or carries one to three substituents selected from the group consisting of cyano, nitro, halogen, $C_1$–$C_6$-alkyl, $C_1$–$C_6$-haloalkyl, $C_1$–$C_6$-alkoxy and $(C_1$–$C_6$-alkoxy)carbonyl;

$R^{21}$ is hydrogen, halogen, $C_1$–$C_6$-alkyl, $C_1$–$C_6$-haloalkyl, $C_1$–$C_6$-alkoxy, $C_1$–$C_6$-haloalkoxy, $C_3$–$C_6$-alkenyloxy, $C_1$–$C_6$-alkylthio, $C_1$–$C_6$-haloalkylthio, $(C_1$–$C_6$-alkyl)carbonyloxy, $(C_1$–$C_6$-haloalkyl)carbonyloxy, $C_1$–$C_6$-alkylsulfonyloxy or $C_1$–$C_6$-haloalkylsulfonyloxy, where the last mentioned 11 radicals are unsubstituted or carry one of the following substituents: hydroxyl, cyano, hydroxycarbonyl, $C_1$–$C_6$-alkoxy, $C_1$–$C_6$-alkylthio, $(C_1$–$C_6$-alkyl)carbonyl, $(C_1$–$C_6$-alkoxy)carbonyl, $(C_1$–$C_6$-alkyl)aminocarbonyl, di$(C_1$–$C_6$-alkyl)aminocarbonyl or $(C_1$–$C_6$-alkyl)carbonyloxy, $(C_1$–$C_6$-alkyl)carbonyl, $(C_1$–$C_6$-haloalkyl)carbonyl, $(C_1$–$C_6$-alkoxy)carbonyl, $(C_1$–$C_6$-alkoxy)carbonyloxy, $(C_1$–$C_6$-alkyl)carbonylthio, $(C_1$–$C_6$-haloalkyl)carbonylthio, $(C_1$–$C_6$-alkoxy)carbonylthio, $C_2$–$C_6$- alkenyl, $C_2$–$C_6$-alkenylthio, $C_3$–$C_6$-alkynyl, $C_3$–$C_6$-alkynyloxy, $C_3$–$C_6$-alkynylthio, ($C_2$–$C_6$-alkynyl)carbonyloxy, $C_3$–$C_6$-alkynylsulfonyloxy, $C_3$–$C_6$-cycloalkyl, $C_3$–$C_6$-cycloalkoxy, $C_3$–$C_6$-cycloalkylthio, ($C_3$–$C_6$-cycloalkyl)carbonyloxy, $C_3$–$C_6$-cycloalkylsulfonyloxy, phenyl, phenoxy, phenylthio, benzoyloxy, phenylsulfonyloxy, phenyl-$C_1$–$C_6$-alkyl, phenyl-$C_1$–$C_6$-alkoxy, phenyl-$C_1$–$C_6$-alkylthio, phenyl-($C_1$–$C_6$-alkyl)carbonyloxy or phenyl-($C_1$–$C_6$-alkyl)sulfonyloxy, where the phenyl rings of the last-mentioned 10 radicals are unsubstituted or carry one to three substituents selected from the group consisting of cyano, nitro, halogen, $C_1$–$C_6$-alkyl, $C_1$–$C_6$-haloalkyl, $C_1$–$C_6$-alkoxy and ($C_1$–$C_6$-alkoxy)carbonyl;

$R^{22}$ having one of the meanings of $R^{19}$;

$R^{23}$, $R^{24}$, $R^{25}$ and $R^{26}$ independently of one another are hydrogen, $C_1$–$C_6$-alkyl, $C_2$–$C_6$-alkenyl, $C_2$–$C_6$-alkynyl, $C_3$–$C_6$-cycloalkyl, $C_1$–$C_6$-haloalkyl, $C_1$–$C_6$-alkoxy-$C_1$–$C_6$-alkyl, ($C_1$–$C_6$-alkyl)carbonyl, ($C_1$–$C_6$-alkoxy)carbonyl, ($C_1$–$C_6$-alkoxy)carbonyl-$C_1$–$C_6$-alkyl, ($C_1$–$C_6$-alkoxy)carbonyl-$C_2$–$C_6$-alkenyl, where the alkenyl chain is unsubstituted or carries one to three halogen and/or cyano radicals, or are $C_1$–$C_6$-alkylsulfonyl, ($C_1$–$C_6$-alkoxy)carbonyl-$C_1$–$C_6$-alkylsulfonyl, phenyl or phenylsulfonyl, where the two phenyl rings are unsubstituted or carry one to three substituents selected from the group consisting of cyano, nitro, halogen, $C_1$–$C_6$-alkyl, $C_1$–$C_6$-haloalkyl, $C_3$–$C_6$-alkenyl, $C_1$–$C_6$-alkoxy and ($C_1$–$C_6$-alkoxy)carbonyl Y is oxygen, sulfur or —N($R^{27}$)—;

$R^{27}$ is hydrogen, hydroxyl, $C_1$–$C_6$-alkyl, $C_3$–$C_6$-alkenyl, $C_3$–$C_6$-alkynyl, $C_3$–$C_7$-cycloalkyl, $C_1$–$C_6$-haloalkyl, $C_1$–$C_6$-alkoxy-$C_1$–$C_6$-alkyl, $C_1$–$C_6$-alkoxy, $C_3$–$C_6$-alkenyloxy, $C_3$–$C_6$-alkynyloxy, $C_3$–$C_6$-cycloalkoxy, $C_5$–$C_7$-cycloalkenyloxy, $C_1$–$C_6$-haloalkoxy, $C_3$–$C_6$-haloalkenyloxy, hydroxy-$C_1$–$C_6$-alkoxy, cyano-$C_1$–$C_6$-alkoxy, $C_3$–$C_6$-cycloalkyl-$C_1$–$C_6$-alkoxy, $C_1$–$C_6$-alkoxy-$C_1$–$C_6$-alkoxy, $C_1$–$C_6$-alkoxy-$C_3$–$C_6$-alkenyloxy, ($C_1$–$C_6$-alkyl)carbonyloxy, ($C_1$–$C_6$-haloalkyl)carbonyloxy, ($C_1$–$C_6$-alkyl)carbamoyloxy, ($C_1$–$C_6$-haloalkyl)carbamoyloxy, ($C_1$–$C_6$-alkyl)carbonyl-$C_1$–$C_6$-alkyl, ($C_1$–$C_6$-alkyl)carbonyl-$C_1$–$C_6$-alkoxy, ($C_1$–$C_6$-alkoxy)carbonyl-$C_1$–$C_6$-alkyl, ($C_1$–$C_6$-alkoxy)carbonyl-$C_1$–$C_6$-alkoxy, $C_1$–$C_6$-alkylthio-$C_1$–$C_6$-alkoxy, di($C_1$–$C_6$-alkyl)amino-$C_1$–$C_6$-alkoxy, phenyl, which is unsubstituted or carries one to three substituents selected from the group consisting of cyano, nitro, halogen, $C_1$–$C_6$-alkyl, $C_1$–$C_6$-haloalkyl, $C_2$–$C_6$-alkenyl, $C_1$–$C_6$-alkoxy and ($C_1$–$C_6$-alkoxy)carbonyl, phenyl-$C_1$–$C_6$-alkoxy, phenyl-$C_3$–$C_6$-alkenyloxy or phenyl-$C_3$–$C_6$-alkynyloxy, where one or two methylene groups of the carbon chains can be replaced by —O—, —S— or —N($C_1$–$C_6$-alkyl)— and where each phenyl ring is unsubstituted or carries one to three substituents selected from the group consisting of cyano, nitro, halogen, $C_1$–$C_6$-alkyl, $C_1$–$C_6$-haloalkyl, $C_2$–$C_6$-alkenyl, $C_1$–$C_6$-alkoxy and ($C_1$–$C_6$-alkoxy)carbonyl, or —N($R^{28}$)$R^{29}$, $R^{28}$ and $R^{29}$ are hydrogen, $C_1$–$C_6$-alkyl, $C_3$–$C_6$-alkenyl, $C_3$–$C_6$-alkynyl, $C_3$–$C_6$-cycloalkyl, $C_1$–$C_6$-haloalkyl, $C_1$–$C_6$-alkoxy-$C_1$–$C_6$-alkyl, ($C_1$–$C_6$-alkyl)carbonyl, ($C_1$–$C_6$-alkoxy)carbonyl, ($C_1$–$C_6$-alkoxy)carbonyl-$C_1$–$C_6$-alkyl, ($C_1$–$C_6$-alkoxy)carbonyl-$C_2$–$C_6$-alkenyl, where the alkenyl chain is unsubstituted or carries one to three halogen and/or cyano radicals, or phenyl which is unsubstituted or carries one to three substituents selected from the group consisting of cyano, nitro, halogen, $C_1$–$C_6$-alkyl, $C_1$–$C_6$-haloalkyl, $C_3$–$C_6$-alkenyl, $C_1$–$C_6$-alkoxy and ($C_1$–$C_6$-alkoxy)carbonyl.

\* \* \* \* \*

UNITED STATES PATENT AND TRADEMARK OFFICE
CERTIFICATE OF CORRECTION

PATENT NO.   : 6,268,311 B1
DATED        : July 31, 2001
INVENTOR(S)  : Menke et al.

It is certified that error appears in the above-identified patent and that said Letters Patent is hereby corrected as shown below:

Column 21, claim 6,
Line 38, "caries" should be -- carries --.

Column 21, claim 8,
Line 59, "caries" should be -- carries --.

Column 23, claim 10,
Line 4, "$C_1$-$C_6$-" should be -- $C_1$-$C_6$- --.

Column 28, claim 16,
Line 43, "$C_1$-$C_6$-"alkylsultonyloxy" should be -- $C_1$-$C_6$-alkylsulfonyloxy --.

Column 32,
Line 36, add claim 17 as follows:

-- 17. The method defined in claim 5, wherein the plants are cotton plants. --

Signed and Sealed this

Nineteenth Day of March, 2002

Attest:

JAMES E. ROGAN
Director of the United States Patent and Trademark Office

Attesting Officer